US007759349B2

(12) United States Patent
Winzenberg et al.

(10) Patent No.: US 7,759,349 B2
(45) Date of Patent: Jul. 20, 2010

(54) CONTROL OF PARASITES IN ANIMALS BY THE USE OF IMIDAZO[1,2-B]PYRIDAZINE DERIVATIVES

(75) Inventors: Kevin N. Winzenberg, Camberwell (AU); Craig L. Francis, Vermont (AU); David G. Sawutz, Maplewood, NJ (US); Ashit Ganguly, Upper Montclair, NJ (US)

(73) Assignee: Schering-Plough Animal Health Corporation, Summit, NJ (US)

( * ) Notice: Subject to any disclaimer, the term of this patent is extended or adjusted under 35 U.S.C. 154(b) by 1502 days.

(21) Appl. No.: 11/019,597

(22) Filed: Dec. 22, 2004

(65) Prior Publication Data
US 2005/0182059 A1 Aug. 18, 2005

Related U.S. Application Data

(60) Provisional application No. 60/533,729, filed on Dec. 31, 2003.

(51) Int. Cl.
*A61K 31/50* (2006.01)
*A61K 31/501* (2006.01)
*C07D 487/00* (2006.01)
(52) U.S. Cl. .................. 514/252.05; 544/236
(58) Field of Classification Search ............ 514/252.05; 544/236
See application file for complete search history.

(56) References Cited

U.S. PATENT DOCUMENTS 3,725,407 A 4/1973 Tomcufcik et al.
3,905,974 A 9/1975 Tomcuecik et al.

FOREIGN PATENT DOCUMENTS

GB 2 065 645 A 7/1981
JP 40-022266 * 10/1965

OTHER PUBLICATIONS

Byrn, et al., "Solid State Chemistry of Drugs," 2nd ed., SSCI, Inc., Chapter 10, p. 232-247, 1999.*
Vippagunta SR, Brittain HG, and Grant D J, "Crystalline solids," Advanced Drug Delivery Reviews, May 2001,48(1), 3-26.*
Barlin, Gordon B., et al., "Imidazo[1,2-b]pyridazines. X Syntheses . . . ," Aust. J. Chem. 45:731-749 (1992).
Barlin, Gordon B., et al., "Imidazo[1,2-b]pyridazines: Syntheses . . . ," J. Heterocyclic Chem. 35:1205-1217 (1998).
Enguehard, Cecile, et al., "Reactivity of 3-Iodoimidazo[1,2-a]pyridines . . . ," J. Org. Chem. 65:6572:6575 (2000).
Enguehard, Cecile, et al., "Reactivity of 6-chloroimidazo[1,2-b]pyridazine . . . ," Synthesis 4:595-600 (2001).
Fabio, P.F., et al., "Synthesis of Carbon-14 . . . ," Journal of Labelling Compounds and Radiopharmaceuticals XV:407-412 (1978).
Grimmett, M.R., et al., "Hetarenes and Related Ring Systems," Science of Synthesis 12:613-678 (2002).
Harrison, PW, et al., "Syntheses, phramacological evaluation . . . ," Eur. J. Med. Chem. 31:651-662 (1996).
Hough, T.L., "Reactions of some 5-substituted . . . ," Journal of Heterocyclic Chemistry 20:1003-1005 (1983).
Kobe, J., et al., "Synthesis of Pyridazine . . . ," Tetrahedron 24:239-245 (1968).
Mourad, Alaa E., et al., "Methyl Imidazo[1,2-b]pyridazine-2-carbamates . . . ," J. Heterocyclic Chem. 29:1583-1592 (Oct.-Nov. 1992).
Mourad, Alaa E., et al., "Synthesis of Imidazo[1,2-b]pyridazines: Fenbendazole . . . ," J. Heterocyclic Chem. 30:1365-1372 (Oct.-Nov. 1993).
Schmitt, Martine, et al., "Imidazo[1,2-b]pyridazines . . . ," Aust. J. Chem. 50:779-785 (1997).
Torgova, S.I., et al., "Liquid-Crystalline . . . ," Journal of Organic Chemistry of the USSR 24:179-183 (1988).
PCT International Search Report dated May 7, 2005 for corresponding PCT Application No. PCT/US2004/043402.

* cited by examiner

*Primary Examiner*—San-ming Hui
*Assistant Examiner*—Paul Zarek

(57) ABSTRACT

Novel imidazo[1,2-b]pyridazine compounds useful for controlling parasites in animals and methods of treatment of parasite infestation in animals using the compounds are disclosed.

6 Claims, No Drawings

CONTROL OF PARASITES IN ANIMALS BY THE USE OF IMIDAZO[1,2-B]PYRIDAZINE DERIVATIVES

CROSS-REFERENCE TO RELATED APPLICATIONS

This application is a non-provisional application that claims priority under 35 U.S.C. §119(e) of provisional application U.S. Ser. No. 60/533,729 filed Dec. 31, 2003, the contents of which are hereby incorporated by reference in their entireties.

BACKGROUND OF THE INVENTION

1. Field of the Invention

The present invention relates to the use of imidazo[1,2-b]pyridazine compounds to control parasites in animals and methods of treating parasite infestation in animals using the compounds.

2. Background

The control of animal parasites is important, especially in the areas of animal husbandry, as well as for companion animals. Existing methods of treatment are being compromised due to the growing resistance to current classes of parasiticides, such as the benzimidazoles and ivermectins. Therefore, there is a need to discover and/or identify new and more effective ways to control parasites of animals.

Derivatives of the imidazo[1,2-b]pyridazine ring system have been reported in the chemical literature and some general synthetic routes to compounds of this type have been reviewed [Hajos, G., Riedl, Z., *Science of Synthesis*, 2002, 12, 613-678; Barlin, G. B., *Journal of Heterocyclic Chemistry*, 1998, 35, 1205]. A range of pharmaceutically useful biological activities has also been reported for some imidazo[1,2-b]pyridazine derivatives [Barlin, G. B., *Journal of Heterocyclic Chemistry*, 1998, 35, 1205]. In the general area of parasite control, however, U.S. Pat. No. 3,905,974 discloses compounds of Formula A:

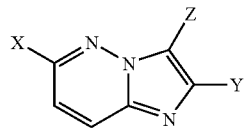

Formula A wherein

X is selected from hydroxy, mercapto, alkoxy ($C_1$-$C_8$), alkylthio ($C_1$-$C_8$), phthalimidoloweralkoxy, phenylloweralkoxy, lower alkoxyloweralkoxy, hydroxyloweralkoxy, loweralkenyloxy, halobenzoylloweralkoxy;

Z is nitro; and

Y is hydrogen or lower alkyl, where "lower" alkyls are those having 1 to 4 carbon atoms. The compounds are mentioned as having anti-protozoal, such as anti-amoebic and anti-trichomonal activity.

Fabio, Lanzilotti and Lang, *Journal of Labelled Compounds and Radiopharmaceuticals*, 1978, XV, 407-412, disclose another compound of Formula A in which X is propoxy, Y is hydrogen and Z is nitro. The compound is said to show amoebicidal and trichomonacidal activity.

Townsend, Mourad and Wise, in *Journal of Heterocyclic Chemistry*, 1992, 29, 1583-1592, describe a set of compounds corresponding to Formula A that were evaluated as potential antifilarial agents. In these compounds X is either $CH_3$, $CO_2H$, $CO_2Me$, $CO_2CH_2CH_2CH_3$, $CO_2CH(CH_3)_2$, $CO_2C(CH_3)_3$, $CONH_2$, 2-thienylcarbonyl, benzoyl or 4-fluorobenzoyl; Y is either tert-butyl or CONHMe; and Z is either hydrogen or bromine.

Townsend, Mourad and Wise, in *Journal of Heterocyclic Chemistry*, 1993, 30, 1365-1375, describe another set of compounds corresponding to Formula A which were evaluated as potential antifilarial agents. In these compounds, X is either phenylthio, phenylsufinyl, phenylsulfonyl, NHCO(2-fluorophenyl), NHCO (3-fluorophenyl), NHCO(4-fluorophenyl), $NH_2$, $NHNH_2$, NHC(=S)O (i-$C_3H_7$), NHC(=O)$SCH_3$; Y is either methyl, tert-butyl, or $NHCO_2CH_3$; and Z is hydrogen.

Despite the forgoing, work has continued in this area in the attempt to find improved methods of treating diseases due to parasites, as well as to identify compounds that are useful in this treatment and for related purposes. The present invention addresses these needs.

The citation of any reference herein should not be construed as an admission that such reference is available as "Prior Art" to the instant application.

SUMMARY OF THE INVENTION

One aspect of the present invention relates to methods of treating parasite infestation in animals. Such methods include administering to an animal in need of such treatment an effective amount of an imidazo[1,2-b]pyridazine compound of the formula:

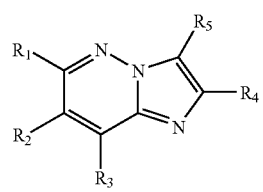

Formula (I)

or a pharmaceutically-acceptable salt thereof or a solvate thereof, wherein:

$R_1$ is hydrogen, ($C_1$-$C_6$)alkoxy, ($C_3$-$C_{10}$)cycloalkoxy, ($C_3$-$C_{10}$)cycloalkyl ($C_1$-$C_6$)alkoxy, (optionally substituted)aryloxy, (optionally substituted)aryl ($C_1$-$C_6$)alkoxy, ($C_1$-$C_6$) alkoxy($C_1$-$C_6$)alkoxy, ($C_1$-$C_6$)alkylsulfanyl, (optionally substituted)arylsulfanyl, (optionally substituted)aryl($C_1$-$C_6$) alkylsulfanyl, ($C_1$-$C_6$)alkyl, ($C_3$-$C_{10}$)cycloalkyl, (optionally substituted)aryl, (optionally substituted)heteroaryl, (optionally substituted)aryl($C_1$-$C_6$)alkyl, heterocyclyl, halo, amino, ($C_1$-$C_6$)alkylamino, ($C_1$-$C_6$)dialkylamino, (optionally substituted) arylamino;

$R_2$, $R_3$ and $R_5$ are independently selected from hydrogen, ($C_1$-$C_6$)alkyl, ($C_1$-$C_6$)alkoxy, (optionally substituted)aryl, ($C_1$-$C_6$)alkylsulfanylmethyl, ($C_1$-$C_6$) dialkylaminomethyl, cyano, halo;

$R_2$ and $R_3$ together may be part of the same fused ring, carbocyclic or heterocyclic, which is optionally substituted; and $R_4$ is (optionally substituted)aryl or (optionally substituted)heteroaryl.

Some preferred compounds in this aspect of the invention include those in which $R_4$ is one of:

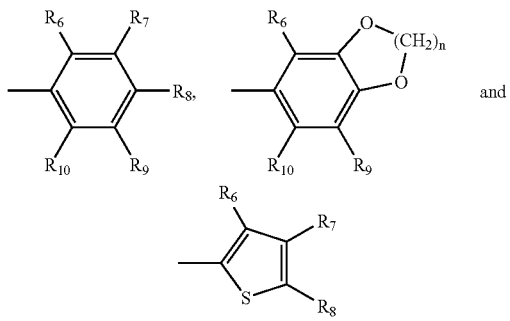

wherein $R_6$, $R_7$, $R_8$, $R_9$ and $R_{10}$ are independently selected from hydrogen, $(C_1-C_6)$alkyl, halo, $(C_1-C_6)$alkoxy, $(C_1-C_6)$alkoxy $(C_1-C_6)$alkoxy, hydroxy$(C_1-C_6)$alkoxy;

$R_5$ and $R_6$ together may be part of the same fused ring, carbocyclic or heterocyclic, aromatic or non-aromatic, which is optionally substituted;

$R_6$ and $R_7$ together may be part of the same fused ring, carbocyclic or heterocyclic, aromatic or non-aromatic, which is optionally substituted;

$R_7$ and $R_8$ together may be part of the same fused ring, carbocyclic or heterocyclic, aromatic or non-aromatic, which is optionally substituted; and n is 1 or 2.

In a preferred embodiment of this type, the imidazo[1,2-b]pyridazine derivative is one of:

Formula (II)

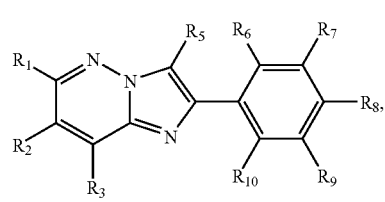

Formula (III)

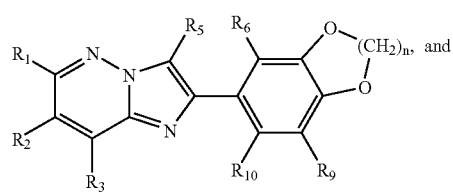

Formula (IV)

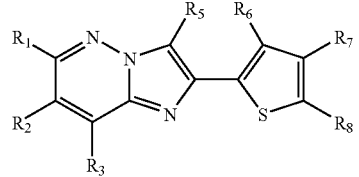

or a pharmaceutically-acceptable salt thereof or a solvate thereof. In still further aspects of the invention, the imidazo [1,2-b]pyridazine derivative is one of the compounds set forth in Table 1.

In a further embodiment of the invention there are provided novel imidazo[1,2-b]pyridazine compounds corresponding to Formula (V)

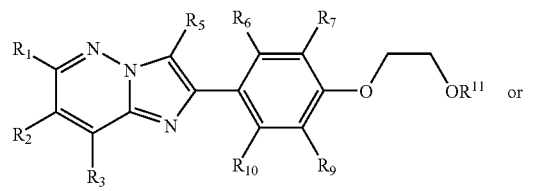

Formula (VI)

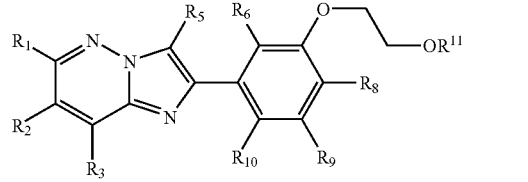

or a pharmaceutically-acceptable salt thereof or a solvate thereof, wherein:

$R_1$ $R_2$, $R_3$ and $R_5$ are the same as that set forth above;

$R_6$, $R_7$, $R_8$, $R_9$ and $R_{10}$ are independently selected from hydrogen, $(C_1-C_6)$alkyl, halo, $(C_1-C_6)$alkoxy, $(C_1-C_6)$alkoxy $(C_1-C_6)$alkoxy, hydroxy $(C_1-C_6)$alkoxy; and $R_{11}$ is hydrogen or $(C_1-C_6)$alkyl.

In another embodiment of the invention there are provided novel imidazo[1,2-b]pyridazine compounds corresponding to the formula:

Formula (VII)

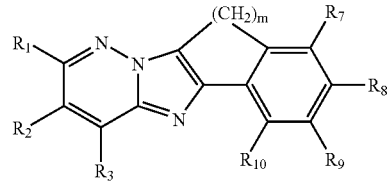

or a pharmaceutically-acceptable salt thereof or a solvate thereof, wherein $R_1$, $R_2$ and $R_3$ are the same as that set forth above;

$R_7$, $R_8$, $R_9$ and $R_{10}$ are independently selected from hydrogen, $(C_1-C_6)$alkyl, halo, $(C_1-C_6)$alkoxy, $(C_1-C_6)$alkoxy$(C_1-C_6)$alkoxy, hydroxy$(C_1-C_6)$alkoxy; and m is 1 or 2.

In one embodiment of the invention, the imidazo[1,2-b] pyridazine derivative is one of the compounds set forth in Tables 2 and 3.

In another embodiment of the invention there are provided methods of treating and/or preventing parasite infestation in animals, comprising administering to an animal in need of such treatment an effective amount of one or more imidazo [1,2-b]pyridazine derivative(s) of formulae (IV), (V), or (VI).

Pharmaceutical compositions containing a novel compound described herein and a pharmaceutically acceptable excipient as well as methods of preparing the compounds described herein are also included as further aspects of the invention.

DETAILED DESCRIPTION OF THE INVENTION

The present invention provides methods of treating parasite infestation in animals through administering effective amounts of the imidazo[1,2-b]pyridazine compounds of the present invention.

As used herein, the following terms are used as defined below unless otherwise indicated.

In this specification "optionally substituted" means that a group may or may not be substituted with one or more groups selected from: alkyl, aryl, cycloalkyl, alkylcycloalkyl, halo, cyano, nitro, haloalkyl, haloaryl, halocycloalkyl, hydroxy, alkoxy, cycloalkoxy, aryloxy, haloalkoxy, haloaryloxy, halocycloalkyloxy, heterocyclyl, heterocyclyloxy, heterocyclylamino, heterocyclylsulfanyl, heterocyclylalkyl, amino, alkylamino, dialklamino, arylamino, acyl, alkenylacyl, arylacyl, acylamino, alkylsulfonyloxy, alkoxycarbonyl, aryloxycarbonyl, aminocarbonyl, alkylsulfanyl, alkylsulfonyl, arylsulfanyl, arylsulfonyl, aminosulfonyl, dialkylaminosulfonyl, alkylcarbonylamino, cycloalkylcarbonylamino, cycloalkenylcarbonylamino, arylcarbonylamino, heterocyclylcarbonylamino, heteroarylcarbonylarnino.

Alkyl used either alone, or in compound words such as alkoxy, alkylsulfanyl, alkylamino, dialkyamino or haloalkyl, denotes straight chain or branched $C_{1-6}$ alkyl, e.g. methyl, ethyl, propyl, isopropyl or the different butyl, pentyl, and hexyl isomers.

Aryl used either alone, or in compound words such as arylalkyl or aryloxy or arylalkoxy, denotes a mono- or polycarbocyclic aromatic ring system, e.g., phenyl or napthyl. All free positions in the aryl ring can be optionally substituted. Heteroaryl represents cyclic aromatic groups of 5 or 6 atoms or bicyclic groups of 11 to 12 atoms having 1, 2, or 3 heteroatoms independently selected from O, S, or N. Such heteroatoms(s) interrupt a carbocyclic ring structure and have a sufficient number of delocalized pi electrons to provide aromatic character, provided that the rings do not contain adjacent oxygen and/or sulfur atoms. For 6-membered heteroaryl rings, carbon atoms can be optionally substituted. All regioisomers are contemplated, e.g., 2-pyridyl, 3-pyridyl and 4-pyridyl. Typical 6-membered heteroaryl groups are pyridyl, pyrimidinyl, pyrazinyl and pyridazinyl. For 5-membered heteroaryl rings, carbon atoms can be optionally substituted. Typical 5-membered heteroaryl rings are furyl, thienyl, pyrrolyl, thiazolyl, isothiazolyl, imidazolyl, pyrazolyl and isoxazolyl. All regioisomers are contemplated, e.g., 2-thienyl and 3-thienyl. Bicyclic groups typically are benzo-fused ring systems derived from the heteroaryl groups named above, e.g., quinolyl, phthalazinyl, quinazolinyl, benzofuranyl, benzothienyl and indolyl.

"Carbocyclic" and "carbocyclyl" denotes a 3 to 10 membered, preferably 5 to 8 membered, ring of carbon atoms. Examples include cyclopentyl, cyclohexyl, phenyl and naphthyl.

Heterocyclyl denotes a group comprising a 3 to 10 membered, preferably 5 to 8 membered, ring containing one to three hetero atoms such as oxygen, nitrogen or sulfur, which may be substituted and/or carry fused rings. Examples of such groups include, pyrrolidinyl, morpholinyl, thiomorpholinyl, or fully or partially hydrogenated thienyl, furanyl, pyrrolyl, thiazolyl, oxazoyl, oxazinyl, thiazinyl, pyridinyl and azepinyl.

Cycloalkyl denotes a mono-or poly-carbocyclic ring system of 3 to 10 carbon atoms, for example cyclopropyl, cyclobutyl, cyclopentyl, cyclohexyl, cycloheptyl. The term cycloalkyloxy denotes the same groups linked through an oxygen atom such as cyclopentyloxy and cyclohexyloxy.

Cycloalkenyl denotes an unsaturated mono- or poly-carbocyclic ring system of 3 to 10 carbons, such as cyclopentenyl and cyclohexenyl.

The term halo, either alone or in compound words such as haloalkyl, denotes fluorine, chlorine, bromine or iodine. Further, when used in compound words such as haloalkyl, the alkyl may be partially halogenated or fully substituted with halogen atoms which may be the same or different. Examples of haloalkyl include —$CH_2CH_2F$, —$CF_2CF_3$ and —$CH_2CHFCl$.

Alkoxy denotes an alkyl group linked to the rest of the molecule via an oxygen atom, for example methoxy, ethoxy, propoxy, isopropoxy, and the different butyloxy, pentyloxy and hexyloxy isomers.

Aryloxy denotes an aryl group linked to the rest of the molecule via an oxygen atom, for example phenoxy. Aryloxyalkyl denotes aryloxy substitution on alkyl. Alkyloxyaryl denotes alkoxy substitution on aryl.

Arylalkoxy denotes aryl substitution on an alkoxy group, e.g. benzyloxy and 2-phenylethoxy.

Alkylsulfanyl denotes alkyl groups linked to the rest of the molecule via a sulfur atom, for example methylsulfanyl, ethylsulfanyl, propylsulfanyl, isopropylsulfanyl, and the different butylsulfanyl, pentylsulfanyl and hexylsulfanyl isomers.

An "effective amount," is the amount or quantity of a compound identified herein that is required to alleviate or reduce parasite numbers in a sample of such parasites, and/or to reduce the numbers of such parasites in and/or on an animal, and/or to inhibit the development of parasite infestation in or on an animal, in whole or in part. This amount is readily determined by observation or detection of the parasite numbers both before and after contacting the sample of parasites with the compound, directly and/or indirectly, e.g., by contacting articles, surfaces, foliage, or animals with the compound. For an in vivo administration of the compound according to the invention, an effective amount is synonymous with a "pharmaceutically effective amount," which is the dose or amount that treats or ameliorates symptoms and/or signs of parasite infection or infestation by the treated animal. This later amount is also readily determined by one of ordinary skill in the art, e.g., by observing or detecting changes in clinical condition or behavior of treated animals, as well as by observing or detecting relative changes in parasite numbers after such treatment. Whether the compound is applied in vivo or ex vivo, the treatment is effective when the parasite count is reduced, after a first application or administration, by an amount ranging from 5% to about 100%. Alternatively, the reduction in parasite count ranges from about 10% to about 95%, relative to the parasite count in an equivalent untreated sample. Accordingly, a "therapeutically effective" amount of an imidazo[1,2-b]pyridazine compound of the present invention may be considered as the amount sufficient to lower parasite numbers in an animal or prevent parasite infestation in an animal.

Compounds of this invention can exist as one or more stereoisomers. The various stereoisomers include enantiomers, diastereomers and geometric isomers. Those skilled in the art will appreciate that one stereoisomer may be more active than the other and how to separate the stereoisomers. Accordingly, the present invention comprises mixtures, individual stereoisomers, and optically active mixtures of the compounds described herein.

Certain compounds of present invention form pharmaceutically acceptable acid addition salts. By way of non-limiting example they can form salts with hydrochloric, hydrobromic, sulfuric, phosphoric, acetic, benzoic, citric, malonic, salicylic, malic, fumaric, oxalic, succinic, tartaric, lactic, gluconic, ascorbic, maleic, aspartic, benzenesulfonic, methane- and ethanesulfonic, hydroxymethane- and hydroxyethanesulfonic acid. The salts are prepared by contacting the free base form with a sufficient amount of the desired acid to produce a salt in the conventional manner. The free base forms may be regenerated by treating the salt with a suitable dilute aqueous base solution such as dilute aqueous NaOH, potassium carbonate, ammonia and sodium bicarbonate. The free base forms differ from their respective salt forms somewhat in certain physical properties, such as solubility in polar solvents, but the acid salts are otherwise equivalent to their respective free base forms for purposes of the invention.

All such acid salts are intended to be pharmaceutically acceptable within the scope of the invention and all acid salts are considered equivalent to the free forms of the corresponding compounds for purposes of the invention.

The compounds of the invention, and the compounds employed in the methods of the invention can also form stable complexes with solvent molecules that remain intact after the non-complexed solvent molecules are removed from the compounds. These complexes are referred to herein as "solvates". Solvates of the compounds of the present invention are also included in the present invention. In a particular embodiment, the solvent molecule is water.

The methods of this invention include the use and/or administration of an above-described compound which has significant parasiticidal activity as an anthelmintic, ectoparasiticide, insecticide and acaricide, in human and animal health and in agriculture.

The disease or group of diseases described generally as helminthiasis is due to infection of an animal host with parasitic worms known as helminths. Helminthiasis is a prevalent and serious economic problem in domesticated animals such as swine, sheep, horses, cattle, goats, dogs, cats and poultry. Among the helminths, the group of worms described as nematodes causes widespread and often times serious infection in various species of animals. The most common genera of nematodes infecting the animals referred to above are *Haemonchus, Trichostrongylus, Ostertagia, Nematodirus, Cooperia, Ascaris, Bunostomum, Oesophagostomum, Chabertia, Trichuris, Strongylus, Trichonema, Dictyocaulus, Capillaria, Heterakis, Toxocara, Ascaridia, Oxyuris, Ancylostoma, Uncinaria, Toxascaris* and *Parascaris*. Certain of these, such as *Nematodirus, Cooperia* and *Oesophagostomum* attack primarily the intestinal tract while others, such as *Haemonchus* and *Ostertagia*, are more prevalent in the stomach while still others such as *Dictyocaulus* are found in the lungs. Still other parasites may be located in other tissues and organs of the body such as the heart and blood vessels, subcutaneous and lymphatic tissue and the like. The parasitic infections known as helminthiasis lead to anaemia, malnutrition, weakness, weight loss, and severe damage to the walls of the intestinal tract and other tissues and organs and, if left untreated, may result in death of the infected host. The compounds described herein have unexpectedly high activity against these parasites, and in addition is also active against Dirofilaria in dogs, Namatospiroides, Syphacia, Aspiculuris in rodents, arthropod ectoparasites of animals and birds such as ticks, mites, lice, fleas, blowfly, in sheep *Lucilia* sp., biting insects and such migrating diperous larvae as *Hypoderma* sp. cattle, *Gastrophilus* in horses, and *Cuterebra* sp. in rodents.

The compounds of the present invention are also useful against parasites which infect humans. The most common genera of parasites of the gastrointestinal tract of man are *Ancylostoma, Necator, Ascaris, Strongyloides, Trichinella, Capillaria, Trichuris,* and *Enterobius*. Other medically important genera of parasites which are found in the blood or other tissues and organs outside the gastrointestinal tract are the filiarial worms such as *Wuchereria, Brugia, Onchocerca* and *Loa, Dracunculus* and extra intestinal stages of the intestinal worms *Strongyloides* and *Trichinella*. These compounds are also of value against arthropods parasitizing man, biting insects and other dipterous pests causing annoyance to man.

By way of further example and not limitation, the compounds and methods of the present invention are presently believed to be effective in the treatment of helminths of veterinary and human importance, including the following classes, families and genera:

| Class | Family | Genus (examples) |
| --- | --- | --- |
| Trematoda | Fasciolidae | *Fasciola* |
| Cestoda | Anoplocephalidae | *Moniezia* |
| " | Dilepididae | *Dipylidium* |
| " | Taeniidae | *Taenia, Echinococcus* |
| Nematoda | Strongyloididae | *Stongyloides* |
| " | Strongylidae | *Strongylus, Oesophagostomum* |
| " | Syngamidae | *Syngamus* |
| " | Trichostrongylidae | *Trichostrongylus, Cooperia, Ostertagia, Haemonchus* |
| " | Heligmonellidae | *Nippostrongylus* |
| " | Dictyocaulidae | *Dictyocaulus* |
| " | Ascarididae | *Ascaris* |
| " | Toxocaridae | *Toxacara* |
| " | Oxyuridae | *Oxyuris* |
| " | Filaridae | *Parafilaria* |
| " | Onchocercidae | *Onchocerca* |
| " | Trichinellidae | *Trichinella* |
| " | Trichuridae | *Trichuris* |
| " | Capillariidae | *Capillaria* |

The inventive compounds are also active against household pests such as the cockroach, *Blatella* sp., clothes moth, *Tineola* sp., carpet beetle, *Attagenus* sp., and the housefly *Musca domestica*.

The inventive compounds are also useful against insect pests of stored grains such as *Tribolium* sp., *Tenebrio* sp. and of agricultural plants such as 2 spider mites, (*Tetranychus* sp.), aphids, (*Acyrthiosiphon* sp.); against migratory orthopterans such as locusts and immature stages of insects living on plant tissue. The compounds are useful as a nematocide for the control of soil nematodes and plant parasites such as *Meloidogyne* spp. which may be of importance in agriculture. The inventive compounds are active against other plant pests such as the southern army worm and Mexican bean beetle larvae.

It will be understood by those of ordinary skill that the methods and compounds of the present invention are useful in treating not only those diseases specifically mentioned but also those which are known to be within the helminthiasis class.

The inventive compounds may be administered orally in a unit dosage form such as a capsule, bolus or tablet, or as a liquid drench where used as an anthelmintic in mammals. The drench is normally a solution, suspension or dispersion of the active ingredient usually in water together with a suspending agent such as bentonite and a wetting agent or like excipient. Generally, the drenches also contain an antifoaming agent.

Drench formulations generally contains from about 0.001 to 0.5% by weight of the active compound. Preferred drench formulations may contain from 0.01 to 0.1% by weight. The capsules and boluses comprise the active ingredient admixed with a carrier vehicle such as starch, talc, magnesium stearate, or di-calcium phosphate.

Where it is desired to administer the inventive compounds in a dry, solid unit dosage form, capsules, boluses or tablets containing the desired amount of active compound usually are employed. These dosage forms are prepared by intimately and uniformly mixing the active ingredient with suitable finely divided diluents, fillers, disintegrating agents and/or binders such as starch, lactose, talc, magnesium stearate, vegetable gums and the like. Such unit dosage formulations may be varied widely with respect to their total weight and content of the antiparasitic agent depending upon factors such as the type of host animal to be treated, the severity and type of infection and the weight of the host. When the active compound is to be administered via an animal feedstuff, it is intimately dispersed in the feed or used as a top dressing or in the form of pellets which may then be added to the finished feed or optionally fed separately. Alternatively, the antiparasitic compounds of our invention may be administered to animals parenterally, for example, by intraruminal, intramuscular, intratracheal, or subcutaneous injection in which event the active ingredient is dissolved or dispersed in a liquid carrier vehicle. For parenteral administration, the active material is suitably admixed with an acceptable vehicle, preferably of the vegetable oil variety such as peanut oil, cotton seed oil and the like. Other parenteral vehicles such as organic preparations using solketal, glycerol formal, and aqueous parenteral formulations are also used. The selected inventive compound is dissolved or suspended in the parenteral formulation for administration; such formulations generally contain from 0.005 to 5% by weight of the active compound.

Although the antiparasitic agent of this invention finds its primary use in the treatment and/or prevention of helminthiasis, they are also useful in the prevention and treatment of diseases caused by other parasites, for example, arthropod parasites such as ticks, lice, fleas, mites and other biting insects in domesticated animals and poultry. It is also effective in treatment of parasitic diseases that occur in other animals including humans. The optimum amount to be employed for best results will, of course, depend upon the particular compound employed, the species of animal to be treated and the type and severity of parasitic infection or infestation. Generally, good results are obtained with the compounds of the present invention by the oral administration of from about 0.001 to 10 mg per kg of animal body weight, such total dose being given at one time or in divided doses over a relatively short period of time such as 1-5 days. With the disclosed compounds of the invention, excellent control of such parasites is obtained in animals by administering from about 0.025 to 0.5 mg per kg of body weight in a single dose. Repeat treatments are given as required to combat re-infections and are dependent upon the species of parasite and the husbandry techniques being employed. The techniques for administering these materials to animals are known to those skilled in the veterinary field. The exact amount of the inventive compound given will of course depend on several factors including the specific compound selected, the animal being treated, the parasite(s) infecting the animal, severity of infection, etc. and all such factors being considered by the artisan in calculating the required effective dose without undue experimentation.

When the compounds described herein are administered as a component of the feed of the animals, or dissolved or suspended in the drinking water, compositions are provided in which the active compound or compounds are intimately dispersed in an inert carrier or diluent. By inert carrier is meant one that will not react with the antiparasitic agent and one that may be administered safely to animals. Preferably, a carrier for feed administration is one that is, or may be, an ingredient of the animal ration.

Suitable compositions include feed premixes or supplements in which the active ingredient is present in relatively large amounts and which are suitable for direct feeding to the animal or for addition to the feed either directly or after an intermediate dilution or blending step. Typical carriers or diluents suitable for such compositions include, for example, distillers' dried grains, corn meal, citrus meal, fermentation residues, ground oyster shells, wheat shorts, molasses solubles, corn cob meal, edible bean mill feed, soya grits, crushed limestone and the like. The active inventive compounds are intimately dispersed throughout the carrier by methods such as grinding, stirring, milling or tumbling. Compositions containing from about 0.005 to 2.0% by weight of the active compound are particularly suitable as feed premixes. Feed supplements, which are fed directly to the animal, contain from about 0.0002 to 0.3% by weight of the active compounds.

Such supplements are added to the animal feed in an amount to give the finished feed the concentration of active compound desired for the treatment and control of parasitic diseases. Although the desired concentration of active compound will vary depending upon the factors previously mentioned as well as upon the particular inventive derivative employed, the compound described in this invention is usually fed at concentrations of between 0.00001 to 0.002% in the feed in order to achieve the desired antiparasitic result. The compounds of this invention are also useful in combating agricultural pests that inflict damage upon crops while they are growing or while in storage. The compound is applied using known techniques as sprays, dusts, emulsions and the like, to the growing or stored crops to effect protection from such agricultural pests.

In some aspects of the invention, the compounds of the invention can be made using techniques apparent to those of ordinary skill in the art and/or by using the methods described in some of the chemical literature references given below. In other aspects, the procedures described in the reaction schemes and methods are described below. Some of the compounds useful in this invention are also exemplified by the following preparative examples, which should not be construed to limit the scope of the disclosure. Alternative mechanistic pathways and analogous structures within the scope of the invention may be apparent to those skilled in the art.

Methods of synthesis of many of the compounds of Formula (I) wherein $R_1$ is $(C_1-C_6)$alkoxy, $(C_3-C_{10})$cycloalkoxy, $(C_3-C_{10})$cycloalkyl$(C_1-C_6)$alkoxy, (optionally substituted) aryloxy, (optionally substituted)aryl$(C_1-C_6)$alkoxy, $(C_1-C_6)$alkoxy$(C_1-C_6)$alkoxy generally commence from 3-amino-6-chloropyridazine derivatives of Formula 8 as shown in Scheme 1:

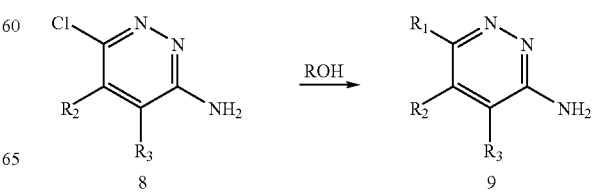

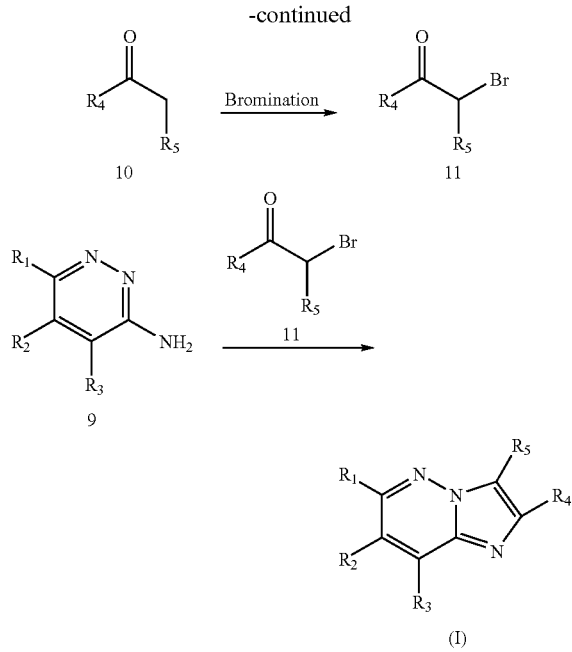

Thus, by way of non-limiting example, reaction of a 3-amino-6-chloropyridazine derivative of Formula 8 with an alkali metal salt of an appropriate alcohol or phenol affords compounds of Formula 9 wherein $R_1$ is $(C_1-C_6)$alkoxy, $(C_3-C_{10})$cycloalkoxy, $(C_3-C_{10})$cycloalkyl$(C_1-C_6)$alkoxy, (optionally substituted) aryloxy, (optionally substituted)aryl$(C_1-C_6)$ alkoxy, $(C_1-C_6)$alkoxy $(C_1-C_6)$alkoxy. Bromination of ketones of the general Formula 10 wherein $R_4$ is optionally substituted aryl or optionally substituted heteroaryl and $R_5$ is hydrogen or $(C_1-C_6)$alkyl affords the corresponding α-bromoketone derivatives of Formula 11. Reaction of the α-bromoketone derivative of Formula 11 with the aminopyridazine of Formula 9 in the presence of a base such as sodium bicarbonate affords compounds of Formula (I) wherein $R_1$ is $(C_1-C_6)$alkoxy, $(C_3-C_{10})$cycloalkoxy, $(C_3-C_{10})$cycloalkyl$(C_1-C_6)$ alkoxy, (optionally substituted) aryloxy, (optionally substituted)aryl$(C_1-C_6)$alkoxy, $(C_1-C_6)$alkoxy $(C_1-C_6)$ alkoxy, and $R_5$ is hydrogen or $(C_1-C_6)$alkyl. See Examples 1, 3, 4, 5, 6 and 7, below.

In another aspect of the invention, a method for preparing a compound of Formula (I) wherein $R_1$ is $(C_1-C_6)$alkoxy, $(C_3-C_{10})$cycloalkoxy, $(C_3-C_{10})$cycloalkyl $(C_1-C_6)$alkoxy, (optionally substituted)aryloxy, (optionally substituted)aryl $(C_1-C_6)$ alkoxy, $(C_1-C_6)$alkoxy$(C_1-C_6)$alkoxy, and $R_5$ is a halogen (selected from bromo, chloro or iodo), involves treatment of the corresponding compound of Formula (I) wherein $R_5$ is hydrogen with the appropriate N-halosuccinimide using the procedures of Kobe, Stanovnik and Tišler, *Tetrahedron*, 1968, 24, 239-245 ($R_5$=Br, Cl) or Gueiffier & co-workers, *Journal of Organic Chemistry.*, 2000, 65, 6572-6575 ($R_5$=I). See Examples 8, 9, and 10, below.

Another method for preparing a compound of Formula 1 wherein $R_1$ is $(C_1-C_6)$alkoxy, $(C_3-C_{10})$cycloalkoxy, $(C_3-C_{10})$ cycloalkyl $(C_1-C_6)$alkoxy, (optionally substituted)aryloxy, (optionally substituted)aryl $(C_1-C_6)$alkoxy, $(C_1-C_6)$alkoxy $(C_1-C_6)$alkoxy, and $R_5$ is cyano involves treatment of the corresponding compound of Formula (I) wherein $R_5$ is a halogen (selected from bromo, chloro or iodo) with cuprous cyanide using the procedures of Torgova, Abolin, Roitman, Karamysheva and Ivaschenko, *Journal of Organic Chemistry of the USSR (Engl. Transl.)*, 1988, 24, 179-183 or Hough, *Journal of Heterocyclic Chemistry*, 1983, 20, 1003-1005. See, Example 11, below.

Another method for preparing a compound of Formula (1) wherein $R_1$ is $(C_1-C_6)$alkoxy, $(C_3-C_{10})$cycloalkoxy, $(C_3-C_{10})$ cycloalkyl$(C_1-C_6)$alkoxy, (optionally substituted)aryloxy, (optionally substituted)aryl$(C_1-C_6)$alkoxy, $(C_1-C_6)$alkoxy $(C_1-C_6)$alkoxy, and $R_5$ is dialkylaminomethyl group involves treatment of the corresponding compound of Formula (I) wherein $R_5$ is hydrogen with a dialkylamine and formaldehyde using the procedure of Barlin and co-workers, *Australian Journal of Chemistry*, 1992, 45, 731-749 and 1997, 50, 779-785. See Example 12, below.

A method for preparing a compound of Formula (I) wherein $R_1$ is $(C_1-C_6)$alkoxy, $(C_3-C_{10})$cycloalkoxy, $(C_3-C_{10})$ cycloalkyl$(C_1-C_6)$alkoxy, aryloxy, aryl$(C_1-C_6)$alkoxy, $(C_1-C_6)$alkoxy$(C_1-C_6)$alkoxy and $R_5$ is an (optionally substituted) aryl or (optionally substituted) heteroaryl group involves treatment of the corresponding compound of Formula (I) wherein $R_5$ is a halogen (selected from bromo, chloro or iodo) with an (optionally substituted)arylboronic acid or a (optionally substituted)heteroarylboronic acid, a base and a palladium catalyst using the procedures of Gueiffier & co-workers, *Journal of Organic Chemistry*, 2000, 65, 6572-6575 and *Synthesis*, 2001, No.4, 595-600. See Example 13, below.

Methods of synthesis of many of the compounds of Formula 1 wherein $R_1$ is $(C_1-C_6)$alkyl, $(C_3-C_{10})$cycloalkyl, (optionally substituted)aryl, (optionally substituted)heteroaryl, (optionally substituted)aryl$(C_1-C_6)$alkyl generally commence from 3-amino-6-chloropyridazine derivatives of Formula 8 by reaction with α-bromoketone derivatives of Formula 11 in the presence of a base such as sodium bicarbonate to afford compounds of Formula 12 which are then reacted with organometallic reagents such as Grignard reagents or organolithium reagents as shown in Scheme 2:

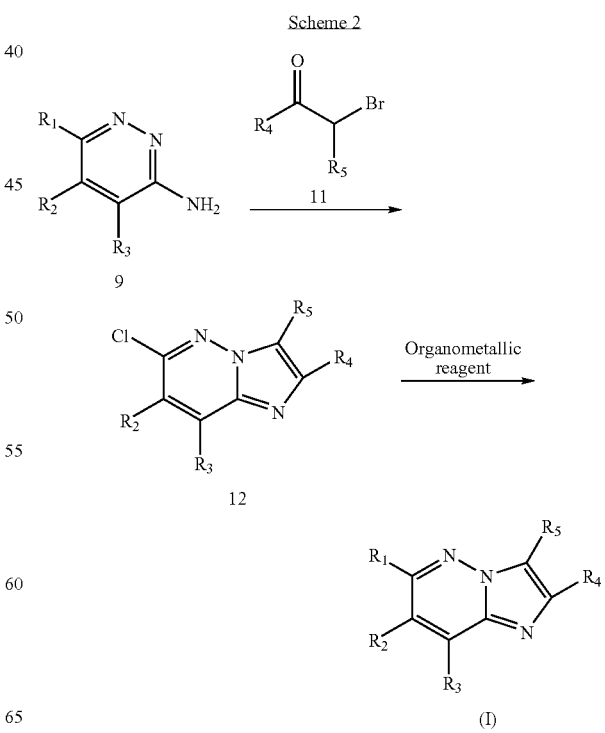

See also Example 14, below.

Compounds of Formula (I) wherein $R_1$ is amino, $(C_1-C_6)$alkylamino, $(C_1-C_6)$dialkylamino, (optionally substituted) arylamino can be prepared from compounds of Formula 12 by reaction with ammonia or with the appropriate alkylamine, dialkylamine or (optionally substituted)arylamine as shown in Scheme 3:

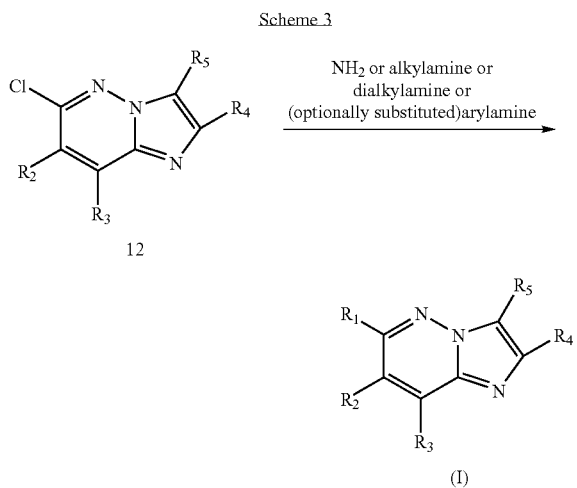

See, Example 15, below.

Compounds of Formula 2 wherein $R_5$ and $R_6$ together may be part of the same fused ring, carbocyclic or heterocyclic, aromatic or non-aromatic, which is optionally substituted, can be prepared by the reaction of compounds of Formula 9 with cyclic α-bromoketones as exemplified by the preparation of the compound of Example 16 and 17.

Methods of synthesis of many of the compounds of Formula (I) wherein $R_1$ is $(C_1-C_6)$alkylsulfanyl, (optionally substituted)arylsulfanyl, (optionally substituted)aryl $(C_1-C_6)$alkylsulfanyl, generally commence from 3-amino-6-chloropyridazine derivatives of Formula 8 as shown in Scheme 4:

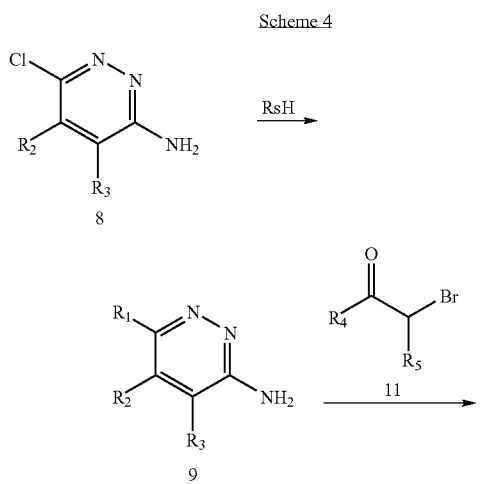

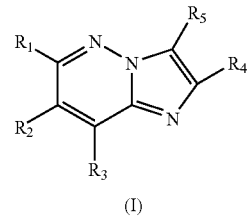

Thus, reaction of a 3-amino-6-chloropyridazine derivative of Formula 8 with an alkali metal salt of a thiol affords a compound of Formula 9, wherein $R_1$ is $(C_1-C_6)$alkylsulfanyl, arylsulfanyl, aryl$(C_1-C_6)$alkylsulfanyl, which is reacted with a α-bromoketone derivative of Formula 11 in the presence of a base such as sodium bicarbonate to afford a compound of Formula (I) wherein $R_1$ is $(C_1-C_6)$alkylsulfanyl, arylsulfanyl, aryl$(C_1-C_6)$alkylsulfanyl. See Example 18, below.

Routes of Administration

As used herein, "administer" or "administration" refers to the delivery of a compound, salt or prodrug of the present invention or of a pharmaceutical composition containing a compound, salt or prodrug of this invention to an organism for the purpose of treating or preventing a parasite infestation in animals.

Suitable routes of administration may include, without limitation, oral, rectal, topical, transmucosal, intramuscular, subcutaneous, intramedullary, intrathecal, direct intraventricular, intravenous, intravitreal, intraperitoneal, intranasal, aural or intraocular. The preferred routes of administration are oral and parenteral.

Alternatively, one may administer the compound in a local rather than systemic manner, for example, by preparation as a salve or topically applied formulation that is applied directly to the infected area or by injection of the compound directly into infected tissue. In either case, a sustained release formulation may be used.

Thus, administration of the compounds of the invention, or their pharmaceutically acceptable salts, in pure form or in an appropriate pharmaceutical composition, can be carried out via any of the accepted modes of administration or agents for serving similar utilities. The routes of administration can be any known to those of ordinary skill. The inventive compounds are given to those in need thereof in any art recognized form, i.e. solid, semi-solid, lyophilized powder, or liquid dosage forms, such as for example, tablets, suppositories, pills, soft elastic and hard gelatin capsules, powders, solutions, suspensions, or aerosols, or the like, in unit or multi-dosage forms suitable for simple administration of precise dosages. The compositions will include a conventional pharmaceutical carrier or excipient and a compound of the invention as the active agent, and, in addition, may include other medicinal agents, pharmaceutical agents, carriers, adjuvants, etc.

Composition/Formulation

Pharmaceutical compositions of the present invention may be manufactured by processes well known in the art, e.g., using a variety of well-known mixing, dissolving, granulating, dragee-making, levigating, emulsifying, encapsulating, entrapping or lyophilizing processes. The compositions may be formulated in conjunction with one or more physiologically acceptable carriers comprising excipients and auxiliaries which facilitate processing of the active compounds into preparations which can be used pharmaceutically. Proper formulation is dependent upon the route of administration chosen.

For injection, including, without limitation, intravenous, intramusclular and subcutaneous injection, the compounds of the invention may be formulated in aqueous solutions, preferably in physiologically compatible buffers known to those of ordinary skill, as well as other excipients or other materials known to those of ordinary skill. For transmucosal administration, penetrants appropriate to the barrier to be permeated are used in the formulation. Such penetrants are generally known in the art.

For oral administration, the compounds can be formulated by combining the active compounds with pharmaceutically acceptable carriers well-known in the art. Such carriers enable the compounds of the invention to be formulated as tablets, pills, lozenges, dragees, capsules, liquids, gels, syrups, pastes, slurries, solutions, suspensions, concentrated solutions and suspensions for diluting in the drinking water of a patient, premixes for dilution in the feed of a patient, and the like, for oral ingestion by a patient. Pharmaceutical preparations for oral use can be made using a solid excipient, optionally grinding the resulting mixture, and processing the mixture of granules, after adding other suitable auxiliaries if desired, to obtain tablets or dragee cores. Useful excipients are, in particular, fillers such as sugars, including lactose, sucrose, mannitol, or sorbitol, cellulose preparations such as, for example, maize starch, wheat starch, rice starch and potato starch and other materials such as gelatin, gum tragacanth, methyl cellulose, hydroxypropylmethylcellulose, sodium carboxymethylcellulose, and/or polyvinylpyrrolidone (PVP). If desired, disintegrating agents may be added, such as cross-linked polyvinyl pyrrolidone, agar, or alginic acid. A salt such as sodium alginate may also be used.

Dragee cores are provided with suitable coatings. For this purpose, concentrated sugar solutions may be used which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical compositions that can be used orally include push-fit capsules made of gelatin, as well as soft, sealed capsules made of gelatin and a plasticizer, such as glycerol or sorbitol. The push-fit capsules can contain the active ingredients in admixture with a filler such as lactose, a binder such as starch, and/or a lubricant such as talc or magnesium stearate and, optionally, stabilizers. In soft capsules, the active compounds may be dissolved or suspended in suitable liquids, such as fatty oils, liquid paraffin, or liquid polyethylene glycols. Stabilizers may be added in these formulations, also.

For administration by inhalation, the compounds of the present invention can conveniently be delivered in the form of an aerosol spray using a pressurized pack or a nebulizer and a suitable propellant, e.g., without limitation, dichlorodifluoromethane, trichlorofluoromethane, dichlorotetrafluoroethane or carbon dioxide. In the case of a pressurized aerosol, the dosage unit may be controlled by providing a valve to deliver a metered amount. Capsules and cartridges of, for example, gelatin for use in an inhaler or insufflator may be formulated containing a powder mix of the compound and a suitable powder base such as lactose or starch.

The compounds may also be formulated for parenteral administration, e.g., by bolus injection or continuous infusion. Formulations for injection may be presented in unit dosage form, e.g., in ampoules or in multi-dose containers. Useful compositions include, without limitation, suspensions, solutions or emulsions in oily or aqueous vehicles, and may contain adjuncts such as suspending, stabilizing and/or dispersing agents. Pharmaceutical compositions for parenteral administration include aqueous solutions of a water soluble form, such as, without limitation, a salt, of the active compound. Additionally, suspensions of the active compounds may be prepared in a lipophilic vehicle. Suitable lipophilic vehicles include fatty oils such as sesame oil, synthetic fatty acid esters such as ethyl oleate and triglycerides, or materials such as liposomes. Aqueous injection suspensions may contain substances that increase the viscosity of the suspension, such as sodium carboxymethyl cellulose, sorbitol, or dextran. Optionally, the suspension may also contain suitable stabilizers and/or agents that increase the solubility of the compounds to allow for the preparation of highly concentrated solutions. Alternatively, the active ingredient may be in powder form for constitution with a suitable vehicle, e.g., sterile, pyrogen-free water, before use.

The compounds may also be formulated in rectal compositions such as suppositories or retention enemas, using, e.g., conventional suppository bases such as cocoa butter or other glycerides.

In addition to the formulations described previously, the compounds may also be formulated as depot preparations. Such long acting formulations may be administered by implantation (for example, subcutaneously or intramuscularly) or by intramuscular or subcutaneous injection. A compound of this invention may be formulated for this route of administration with suitable polymeric or hydrophobic materials (for instance, in an emulsion with a pharmacologically acceptable oil), with ion exchange resins, or as a sparingly soluble derivative such as, without limitation, a sparingly soluble salt.

Other delivery systems for relatively hydrophobic pharmaceutical compounds may be employed. Liposomes and emulsions are well-known examples of delivery vehicles or carriers for hydrophobic drugs. In addition, organic solvents such as dimethylsulfoxide may be used, if needed.

Additionally, the compounds may be delivered using a sustained-release system, such as semi-permeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the particular compound, additional stabilization strategies may be employed.

Pharmaceutical compositions useful herein also may comprise solid or gel phase carriers or excipients. Examples of such carriers or excipients include, but are not limited to, calcium carbonate, calcium phosphate, various sugars, starches, cellulose derivatives, gelatin, and polymers such as polyethylene glycols.

EXAMPLES

The following examples serve to provide further appreciation of the invention but are not meant in any way to restrict the effective scope of the invention.

Example 1

Preparation of 2-[4-(2-Methoxyethoxy)phenyl]-6-propoxyimid-azo[1,2-b]pyridazine (Compound 63)

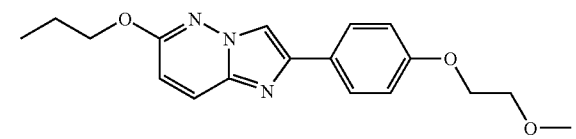

a) 6-Propoxypyridazin-3-amine was prepared by the procedure of Barlin et al, *European Journal of Medicinal Chemistry*, 1996, 31, 651-662.

b) 2-Bromo-1-[4-(2-methoxyethoxy)phenyl]ethanone was prepared by the procedure of Ostermayer, Zimmermann and Fuhrer, UK Patent Application GB 2 065 645 A.

c) A stirred mixture of 6-propoxypyridazin-3-amine (4.50 g, 29.4 mmol), 2-bromo-1-[4-(2-methoxyethoxy)phenyl]ethanone (8.03 g, 29.4 mmol) and ethanol (280 mL) was heated under reflux for 2.5 hours. The mixture was cooled and sodium bicarbonate (2.50 g, 30 mmol) added. The mixture was stirred at room temperature for 15 hours, heated under reflux for 1 hour, then cooled and evaporated. The residue was extracted with chloroform (150 mL) and the extract washed with saturated, aqueous, sodium chloride solution (50 mL), dried (MgSO$_4$) and evaporated. The residue was purified by flash chromatography on silica gel. Elution with 1-2% methanol in dichloromethane afforded a green/brown solid. Treatment with decolourising charcoal in diethyl ether solution (three times) and recrystallization from cyclohexane gave Compound 63 (3.95 g, 41%) as pale green crystals. M.p. 82.5-84° C. $^1$H n.m.r. (CDCl$_3$) δ 1.06, t, J=7.2 Hz, 3H; 1.75-1.94, m, 2H; 3.47, s, 3H; 3.74-3.81, m, 2H; 4.14-4.21, m, 2H; 4.27, t, J=6.6 Hz, 2H; 6.68, d, J=9.3 Hz, 1H; 7.00, d, J=8.8 Hz, 2H; 7.76-7.88, m, 3H; 7.94, s, 1H. Mass spectrum (APCI+) m/z 328 (M+H, 100%).

Example 2

Preparation of 2-[4-(2-Ethoxy)phenyl]-6-phenylimidazo[1,2-b]pyridazine (Compound 79)

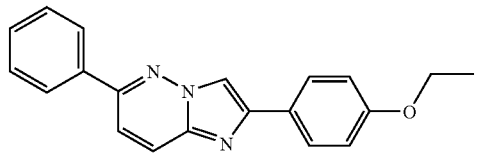

a) 6-Phenylpyridazin-3-amine was prepared by the procedure of Grundmann, *Chemische Berichte*, 1948, 81, 1-12.

b) A stirred mixture of 6-phenylpyridazin-3-amine (260 mg), 2-bromo-1-(4-ethoxyphenyl)ethanone (540 mg) and ethanol (15 mL) was heated under reflux for 5 hours. The mixture was cooled and sodium hydrogen carbonate (92 mg) added. The mixture was stirred and heated under reflux for 3 hours, then cooled. The precipitate that formed was filtered off and dissolved in chloroform (10 mL). The chloroform solution was filtered through cottonwool and evaporated to afford Compound (79) as a pale yellow solid. $^1$H n.m.r. (CDCl$_3$) δ 1.43, t, 3H; 4.13, q, 2H; 7.02, d, 2H; 7.42-7.58, m 4H; 7.82-8.05, m, 5H; 8.20, s, 1H. Mass spectrum (APCI+) m/z 316 (M+H, 100%).

Example 3

Preparation of 2-[4-(2-Methoxyethoxy)phenyl]-6-cyclopropylmethoxyimidazo[1,2-b]pyridazine (Compound 75) and 2-[4-(2-Hydroxyethoxy)phenyl]-6-cyclopropylrnethoxyimidazo[1,2-b]pyridazine (Compound 76)

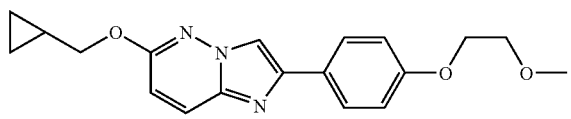

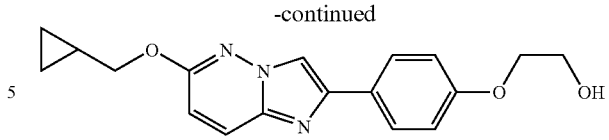

a) Sodium (127 mg) was added to a stirred cyclopropylmethanol (5 g). After the sodium had dissolved, 6-chloropyridazin-3-amine (0.648 g) was added and the mixture was heated to 170° in a glass pressure vessel with magnetic stirring for 23 h. The cooled reaction mixture was diluted with water and extracted with chloroform (3×50 mL). The combined extracts were dried (sodium sulfate) and evaporated to afford crude 6-cyclopropylmethoxypyridazin-3-amine (716 mg). $^1$H n.m.r. (CDCl$_3$) δ 0.27-0.38, m, 2H; 0.52-0.66, m, 2H; 1.18-1.38, m, 1H; 4.18, d, 2H; 4.47 broad s, 2H; 7.78, AB q, 2H.

b) A stirred mixture of 6-cyclopropylmethoxypyridazin-3-amine (165 mg, 1 mmol) and 2-bromo-1-[4-(2-methoxyethoxy)phenyl]ethanone (273 mg, 1 mmol) in ethanol (10 mL) was heated under reflux for 3 hours. Sodium hydrogen carbonate (84 mg, 1 mmol) was added and the mixture was refluxed for another 2 hours. The mixture was evaporated. The residue was extracted with chloroform (150 mL) and the extract washed with saturated, aqueous, sodium chloride solution (50 mL), dried (MgSO$_4$) and evaporated. The residue was purified by flash chromatography on silica gel. Elution with 1-3% methanol in dichloromethane afforded Compound 75 (101 mg). $^1$H n.m.r. (CDCl$_3$) δ 0.22-0.34, m, 2H; 0.62-0.52, m, 2H; 1.07-1.32, m, 1H; 3.25, s, 3H; 3.61-3.68, m, 2H; 3.98-4.12, m, 4H; 6.58, d, 1H; 6.90, d, 2H; 7.65, d, 1H; 7.70, d, 2H; 7.80, s, 1H. Mass spectrum (APCI+) m/z 340 (M+H, 100%). Further elution afforded Compound 76 (62 mg). $^1$H n.m.r. (CDCl$_3$) δ 0.24-0.38, m, 2H; 0.52-0.64, m, 2H; 1.15-1.35, m, 1H; 2.25, broad s, 1H; 3.85-3.95, m, 2H; 4.00-4.15, m, 4H; 6.62, d, 1H; 6.88, d, 2H; 7.72, d, 1H; 7.76, d, 2H; 7.84, s, 1H. Mass spectrum (APCI+) m/z 326 (M+H).

Example 4

Preparation of 2-(3,4-Methylendioxyphenyl)-6-cyclopropylmethoxyimidazo[1,2-b]pyridazine (Compound 43)

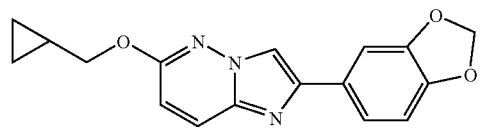

A stirred mixture of 6-cyclopropylmethoxypyridazin-3-amine (110 mg), 2-bromo-1-(3,4-methylenedioxyphenyl)ethanone (162 mg), sodium hydrogen carbonate (84 mg, 1 mmol) and ethanol (5 mL) was heated under reflux for 3 hours. Sodium hydrogen carbonate (56 mg) was added and the mixture was refluxed for a further 0.5 hour. The mixture was evaporated. The residue was extracted with chloroform (50 mL) and the extract washed with saturated, aqueous, sodium chloride solution (50 mL), dried (MgSO$_4$) and evaporated. The residue was purified by flash chromatography on silica gel. Elution with 1-3% methanol in dichloromethane afforded Compound 43 (162 mg). $^1$H n.m.r. (CDCl$_3$) δ 0.33-0.43, m, 2H; 0.62-0.72, m, 2H; 1.22-1.44, m, 1H; 4.13, d, 2H; 6.0, s, 2H; 6.72, d, 1H; 6.86, d, 1H; 7.38, s, 1H; 7.40, d, 1H; 7.78, d, 1H; 7.90, s, 1H.

Example 5

Preparation of 1-Methyl-2-(2-thienyl)-6-cyclopropylmethoxyimidazo[1,2-b]pyridazine (Compound 44)

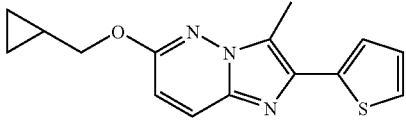

A stirred mixture of 6-cyclopropylmethoxypyridazin-3-amine (165 mg) and 2-bromo-1-(2-thienyl)propan-1-one (*Tetrahedron Letters*, 1981, 22, 4305-4308) (219 mg) in ethanol (10 mL) was heated under reflux for 3 hours. Sodium hydrogen carbonate (84 mg) was added and the mixture was refluxed for a further 2.5 hours. The mixture was evaporated. The residue was extracted with chloroform (50 mL) and the extract washed with saturated, aqueous, sodium chloride solution (50 mL), dried (MgSO$_4$) and evaporated. The residue was purified by flash chromatography on silica gel. Elution with 1% methanol in dichloromethane afforded Compound 44 (190 mg). $^1$H n.m.r. (CDCl$_3$) δ 0.28-0.38, m, 2H; 0.52-0.66, m, 2H; 1.16-1.37, m, 1H; 2.62, s, 3H; 4.12, d, 2H; 6.60, d, 1H; 7.01-7.11, m, 1H; 7.26, d, 1H; 7.34, d, 1H; 7.68, d, 1H.

Example 6

Preparation of 2-(4-Ethoxyphenyl)-5-methyl-6-propoxyimidazo[1,2-b]pyridazine (Compound 33)

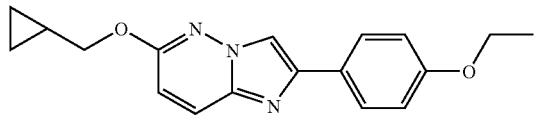

A stirred mixture of 6-cyclopropylmethoxypyridazin-3-amine (165 mg, 1 mmol), 2-bromo-1-(4-ethoxyphenyl)ethanone (243 mg, 1 mmol) and ethanol (10 mL) was heated under reflux for 3 hours. Sodium hydrogen carbonate (84 mg, 1 mmol) was added and the refluxing was continued for another 3 hours. The mixture was evaporated. The residue was extracted with chloroform (50 mL) and the extract washed with saturated, aqueous, sodium chloride solution (50 mL), dried (MgSO$_4$) and evaporated. The residue was purified by flash chromatography on silica gel. Elution with 1% methanol in dichloromethane afforded Compound 33 (140 mg). $^1$H n.m.r. (CDCl$_3$) δ 0.30-0.42, m, 2H; 0.60-0.74, m, 2H; 1.20-1.38, m, 1H; 1.40, t, 3H; 4.04, q, 2H; 4.14, d, 2H; 6.70, d, 1H; 6.96, d, 2H; 7.74, d, 1H; 7.80, d, 2H; 7.88, s, 1H.

Example 7

Preparation of 2-[4-(2-Methoxyethoxy)phenyl]-5-methyl-6-propoxyimidazo[1,2-b]pyridazine (Compound 77) and 2-[4-(2-Hydroxyethoxy)phenyl]-5-methyl-6-propoxyimidazo[1,2-b]pyridazine (Compound 78)

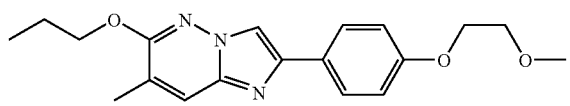

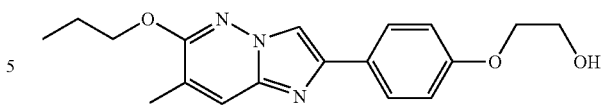

a) Sodium (40 mg) was added to stirred propanol (4 g). After the sodium had dissolved, 6-chloro-5-methylpyridazin-3-amine (200 mg) was added and the mixture was heated to 155° in a glass pressure vessel with magnetic stirring for 24 h. The cooled reaction mixture was diluted with water and extracted with chloroform (3×50 mL). The combined extracts were dried (sodium sulfate) and evaporated to afford crude 5-methyl-6-propyoxypyridazin-3-amine.

b) A stirred mixture of 5-methyl-6-propyloxypyridazin-3-amine (95 mg, 0.57 mmol) and 2-bromo-1-[4-(2-methoxyethoxy)phenyl]ethanone (156 mg, 0.57 mmol) in ethanol (5 mL) was heated under reflux for 3 hours. Sodium hydrogen carbonate (48 mg, 0.57 mmol) was added and the mixture was refluxed for another 2 hours. The mixture was evaporated. The residue was extracted with chloroform (150 mL) and the extract washed with saturated, aqueous, sodium chloride solution (50 mL), dried (MgSO$_4$) and evaporated. The residue was purified by flash chromatography on silica gel. Elution with 1% methanol in dichloromethane afforded Compound 77 (57 mg). $^1$H n.m.r. (CDCl$_3$) δ 1.08, t, 3H; 1.83, sextet, 2H; 2.22, s, 3H; 3.47, s, 3H; 3.72-3.80, m, 2H; 4.10-4.18, m, 2H; 4.27, t, 2H; 6.97, d, 2H; 7.50, s, 1H; 7.82, d, 2H; 7.85, s, 1H. Mass spectrum (APCI+) m/z 342 (M+H, 100%). Further elution afforded Compound 78 (32 mg). $^1$H n.m.r. (CDCl$_3$) δ 1.08, t, 3H; 1.86, sextet, 2H; 2.23, s, 3H; 2.45, broad s, 1H; 3.93-4.05, m, 2H; 4.05-4.17, m, 2H; 6.96, d, 2H; 7.55, s, 1H; 7.82, d, 2H; 7.89, s, 1H. Mass spectrum (APCI+H) m/z 328 (M+).

Example 8

Preparation of 2-[4-(2-Methoxyethoxy)phenyl]-3-chloro-6-propoxyimidazo[1,2-b]pyridazine (Compound 91)

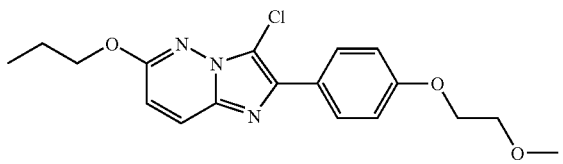

A stirred mixture of 2-[4-(2-methoxyethoxy)phenyl]-6-propoxyimidazo[1,2-b] pyridazine (164 mg, 0.50 mmol), N-chlorosuccinimide (67 mg, 29.4 mmol) and chloroform (3 mL) was heated under reflux for 1.5 hours. The mixture was cooled and washed with saturated aqueous sodium bicarbonate solution, dried (MgSO$_4$) and evaporated. The residue was purified by radial chromatography on silica gel. Elution with 0-2% methanol in dichloromethane afforded Compound 91 (158 mg, 87%) as an off-white solid. $^1$H n.m.r. (CDCl$_3$) δ 1.07, t, J=7.5 Hz, 3H; 1.75-2.0, m, 2H; 3.47, s, 3H; 3.78, t, J=4 Hz, 2H; 4.19, t, J=4 Hz, 2 H; 4.38, t, J=6.5 Hz, 2H; 6.74, d, J=9.5 Hz, 1H; 7.04, d, J=8.5 Hz, 2H; 7.81, d, J=9.5 Hz, 1H; 8.06, d, J=8.5 Hz, 2H. Mass spectrum (APCI+) m/z 362/364 (M+H, 100%).

Example 9

Preparation of 2-[4-(2-Methoxyethoxy)phenyl]-3-iodo-6-propoxyimidazo[1,2-b]pyridazine (Compound 96)

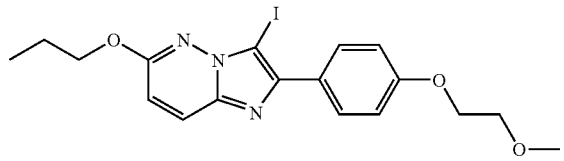

A mixture of 2-[4-(2-methoxyethoxy)phenyl]-6-propoxyimidazo[1,2-b]pyridazine (327 mg, 1.00 mmol), N-iodosuccinimide (225 mg, 1.00 mmol) and acetonitrile (4 mL) was stirred at room temperature for 1.5 hours. The mixture was filtered and the collected solid washed with cold, fresh acetonitrile to afforded Compound 96 (344 mg, 76%) as an off-white solid. $^1$H n.m.r. (CDCl$_3$) δ 1.08, t, J=7.3 Hz, 3H; 1.8-2.0, m, 2H; 3.47, s, 3H; 3.75-3.83, m, 2H; 4.15-4.23, m, 2H; 4.41, t, J=6.6 Hz, 2H; 6.76, d, J=9.5 Hz, 1H; 7.04, d, J=9.3 Hz, 2H; 7.80, d, J=9.9 Hz, 1H; 8.04, d, J=8.7 Hz, 2H. Mass spectrum (APCI+) m/z 454 (M+H, 100%).

Example 10

Preparation of 1-Bromo-2-[4-(2-methoxyethoxy)phenyl]-6-cyclopropylmethoxyimidazo[1,2-b]pyridazine (Compound 88)

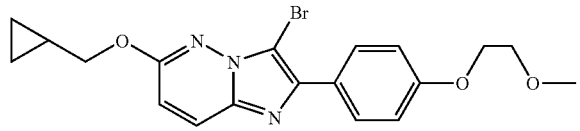

A stirred mixture of 2-[4-(2-methoxyethoxy)phenyl]-6-cyclopropylmethoxyimidazo[1,2-b]pyridazine (40 mg, 0.12 mmol), N-bromosuccinimide (21 mg, 0.12 mmol) and chloroform (1 mL) was heated under reflux for 10 minutes. The mixture was diluted with chloroform, washed with saturated aqueous sodium bicarbonate solution, dried (MgSO$_4$) and evaporated to afford Compound 88 (50 mg) as a fawn coloured solid. $^1$H n.m.r. (CDCl$_3$) δ 0.33-0.40, m, 2H; 0.55-0.68, m, 2H; 1.15-1.20, m, 1H; 3.40, s, 3H; 3.66-3.76, m, 2H; 4.05-4.16, m, 2H; 4.20, d, 2H; 6.72, d, 1H; 7.00, d, 2H; 7.75, d, 1H; 8.00, d, 2H.
Mass spectrum (APCI+) m/z 418/421 (M+H, 100%).

Example 11

Preparation of 2-[4-(2-Methoxyethoxy)phenyl]-3-cyano-6-propoxy-imidazo[1,2-b]pyridazine (Compound 110)

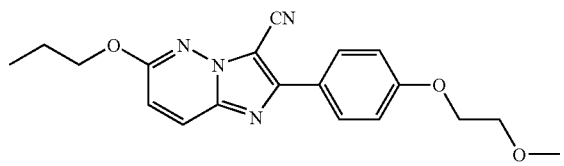

A mixture of 2-[4-(2-methoxyethoxy)phenyl]-3-iodo-6-propoxyimidazo[1,2-b]pyridazine (100 mg, 0.22 mmol), cuprous cyanide (22 mg, 0.24 mmol) and N,N-dimethylformamide (2 mL) was heated at 80° for 22 hours. More CuCN (10 mg) was added and the mixture heated at 100° for 29 hours. Aqueous ferric chloride solution (5%, acidified with HCl) (7 mL) was added and the resulting mixture heated at 60° for 30 minutes. The resulting suspension was filtered and the collected solid washed with saturated, aqueous sodium bicarbonate solution, water (twice) and air-dried overnight. The beige coloured solid was radially chromatographed on silica gel. Elution with 0-1% methanol in dichloromethane provided Compound 110 (50 mg, 64%) as a brilliant white solid. $^1$H n.m.r. (CDCl$_3$) δ 1.06, t, J=7.4 Hz, 3H; 1.76-1.96, m, 2H; 3.47, s, 3H; 3.74-3.82, m, 2H; 4.15-4.22, m, 2H; 4.37, t, J=6.6 Hz, 2H; 6.88, d, J=9.5 Hz, 1H; 7.04, d, J=8.8 Hz, 2H; 7.82, d, J=9.5 Hz, 1H; 8.09, d, J=8.7 Hz, 2H. Mass spectrum (APCI+) m/z 353 (M+H, 100%). Further elution afforded recovered starting material (21 mg, 21%).

Example 12

Preparation of 2-[4-(2-Methoxyethoxy)phenyl]-3-dimethylamino-methyl-6-propoxyimidazo[1,2-b]pyridazine (Compound 98)

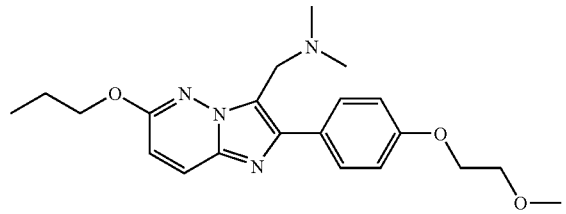

A mixture of 2-[4-(2-methoxyethoxy)phenyl]-6-propoxyimidazo[1,2-b]pyridazine (327 mg, 1 mmol), paraformaldehyde (200 mg, 6.65 mmol), aqueous dimethylamine (40% w/v, 1.0 mL, 8.5 mmol) and acetic acid (3 mL) was heated at 120° for 22 hours. The mixture was cooled and concentrated. The residue was dissolved in chloroform and extracted thrice with dilute (10%) hydrochloric acid. The combined extracts were basified with aqueous sodium hydroxide solution (25%), the resulting suspension chilled in ice and filtered by suction. The collected solid was washed twice with water and dried at the pump to provide Compound 98 (75 mg) as a beige solid. $^1$H n.m.r. (CDCl$_3$) δ 1.07, t, J=7.4 Hz, 3H; 1.76-1.96, m, 2H; 2.32, s, 6H; 3.47, s, 3H; 3.74-3.82, m, 2H; 3.87, s, 2H; 4.14-4.22, m, 2H; 4.32, t, J=7.5 Hz, 2H; 6.66, d, J=9.5 Hz, 1H; 7.03, d, J=8.8 Hz, 2H; 7.77, d, J=10.2 Hz, 1H; 7.98, d, J=8.8 Hz, 2H. Mass spectrum (APCI+) m/z 385 (M+H, 60%), 340 (100).

Example 13

Preparation of 2-[4-(2-Methoxyethoxy)phenyl]-3-phenyl-6-propoxyimidazo[1,2-b]pyridazine (Compound 97)

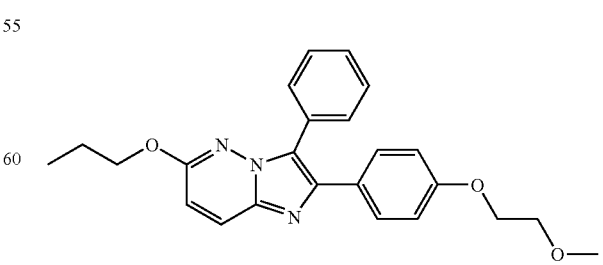

2-[4-(2-Methoxyethoxy)phenyl]-3-iodo-6-propoxyimidazo[1,2-b]pyridazine (100 mg, 0.22 mmol) was dissolved with stirring in 1,2-dimethoxyethane (2.5 mL) under an atmosphere of nitrogen. Phenylboronic acid (30 mg, 0.24 mmol) was added followed by tetrakis(triphenylphosphine)-palladium(0) (20 mg). A solution of sodium hydroxide (18 mg, 0.44 mmol) in water (1 mL) was added. The resulting mixture was heated at 70° for 1 hour then cooled and partitioned between dichloromethane and water. The aqueous layer was extracted with dichloromethane and the combined organics dried and evaporated. The cream coloured solid residue was radially chromatographed on silica gel. Elution with 0-3% methanol in dichloromethane provided Compound 97 (74 mg) as a white solid. $^1$H n.m.r. (CDCl$_3$) δ 1.00, t, J=7.3 Hz, 3H; 1.74-1.86, m, 2H; 3.45, s, 3H; 3.75, t, J=4.3 Hz, 2H; 4.13, t, J=4.3 Hz, 2H; 4.18, t, J=6.3 Hz, 2H; 6.70, d, J=9.5 Hz, 1H; 6.88, d, J=8.4 Hz, 2H; 7.35-7.47, m, 3H; 7.57, d, J=8.3 Hz 2H; 7.62, d, J=6.8 Hz, 2H; 7.82, d, J=9.3 Hz, 1H. Mass spectrum (APCI+) m/z 404 (M+H, 100%).

Example 14

Preparation of 2-[4-(2-Methoxyethoxy)phenyl]-6-butylimidazo[1,2-b]pyridazine (Compound 82)

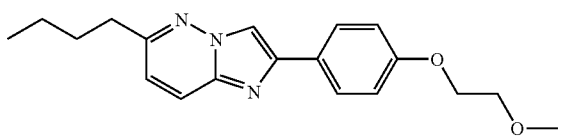

A solution of 2-[4-(2-methoxyethoxy)phenyl]-6-chloroimidazo[1,2-b]pyridazine (304 mg, 1 mmol) in tetrahydrofuran (7 mL) was added with stirring to a solution of butylmagnesium bromide (10 mmol) (prepared from 1-bromobutane (1.37 g, 10 mmol) and magnesium turnings (0.27 g, 11 mmol) and a crystal of iodine in tetrahydrofuran (8 mL)) under an atmosphere of nitrogen. [1,3-Bis(diphenylphosphino)propane] dichloronickel(II) (81 mg, 0.15 mmol) was added and the resulting mixture was stirred at room temperature overnight. Saturated, aqueous ammonium chloride solution was added and the resulting mixture extracted with ether (100 mL). The organic layer was washed with brine (80 mL), dried and evaporated. The residue was radially chromatographed on silica gel. Elution with 1-3% methanol in dichloromethane provided Compound 82 (8 mg) as a brown solid. $^1$H n.m.r. (CDCl$_3$) δ 0.97, t, J=7.3 Hz, 3H; 1.32-1.52, m, 2H; 1.64-1.84, m, 2H; 2.83, t, J=7.5 Hz, 2H; 3.47, s, 3H; 3.72-3.82, m, 2H; 4.12-4.22, m, 2H; 6.92-7.06, m, 3H; 7.86-7.94, m, 3H; 8.10, s, 1H. Mass spectrum (APCI+) m/z 326 (M+H, 100%).

Example 15

Preparation of 2-[4-(2-Methoxyethoxy)phenyl]-6-(N-methyl) butylaminoimidazo[1,2-b]pyridazine (Compound 72)

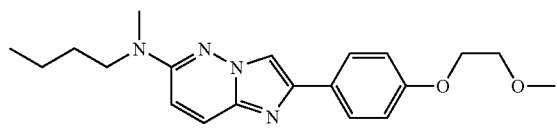

A suspension of 2-[4-(2-methoxyethoxy)phenyl]-6-chloroimidazo[1,2-b]pyridazine (94 mg, 0.31 mmol) in N-methyl butylamine (2.0 mL) in a glass pressure vessel was heated at 160° for 6 h. The reaction mixture was poured into ice water and a solid slowly appeared. The solid was filtered off and air dried. The solid was radially chromatographed on silica. Elution with 1-5% methanol in dichloromethane provided Compound 72 (18 mg) as a brown solid. $^1$H n.m.r. (CDCl$_3$) δ 0.94, t, J=7.3 Hz, 3H; 1.24-1.44, m, 2H; 1.44-1.64, m, 2H; 3.06, s, 3H; 3.40-3.50, m, 2H; 3.48, s, 3H; 3.72-3.80, m, 2H; 4.12-4.20, m, 2H; 6.68, d, J=9 Hz, 1H; 6.98, d, J=9 Hz, 2H; 7.64, d, J=9 Hz, 1H; 7.85, d, J=9 Hz, 2H: 7.90, s, 1H.

Example 16

3-Methoxy-8-propoxy-5,6-dihydro-6b,7,11-triazabenzo[a]fluorene (Compound 121)

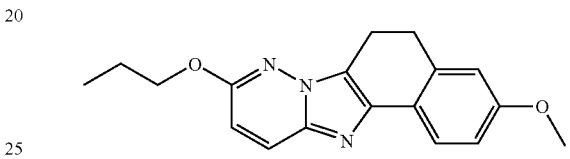

a) 2-Bromo-6-methoxy-3,4-dihydronapthalen-1(2H)-one was prepared by the procedure of Kasturi and Arunachalam, *Canadian Journal of Chemistry*, 1968, 46, 3625-9.

b) A stirred mixture of 6-propoxypyridazin-3-amine (120 mg, 0.78 mmol), 2-bromo-6-methoxy-3,4-dihydronaphtalen-1 (2H)-one (200 mg, 0.78 mmol) in ethanol was heated under reflux for 0.5 hours. The mixture was cooled and sodium bicarbonate (66 mg, 0.78 mmol) added. The mixture was stirred at room temperature for 3 days and evaporated. The residue was extracted with chloroform and the extract washed with saturated, aqueous, sodium chloride solution, dried (MgSO$_4$) and evaporated. The residue was purified by flash chromatography on silica gel. Elution with 1-2% methanol in dichloromethane afforded Compound 121 (30 mg) as a white solid. $^1$H n.m.r. (CDCl$_3$) δ 1.05, t, J=7.4 Hz, 3H; 1.74-1.94, m, 2H; 3.14, s, 4H; 3.82, s, 3H; 4.28, t, J=6.8 Hz, 2H; 6.60, d, J=9.9 Hz, 1H; 6.78-6.89, m, 2H; 7.77, d, J=9.6 Hz, 1H; 7.87, d, J=7.9 Hz, 1H.

Example 17

3-Propoxy-5H-4,4a, 10-triaza-indeno[2,1-a]indene (Compound 123)

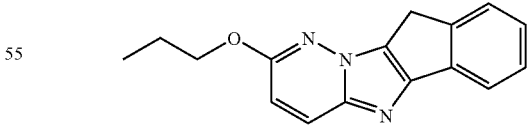

A stirred mixture of 6-propoxypyridazin-3-amine (145 mg) and 2-bromo-1-indanone (200 mg) in ethanol (10 mL) was heated under reflux for 3 hours. The mixture was cooled and sodium bicarbonate (80 mg) was added. The mixture was stirred refluxed for 1 hour and then the ethanol was evaporated. The residue was extracted with chloroform and the extract washed with saturated, aqueous, sodium chloride solution, dried (MgSO$_4$) and evaporated. The residue was purified by flash chromatography on silica gel. Elution with 1-2% methanol in dichloromethane afforded Compound 123 (30 mg) as a white solid. $^1$H n.m.r. (CDCl$_3$) δ 1.12, t, 3H; 1.87, sextet, 2H; 3.85, s, 2H; 4.30, t, 2H; 6.64, d, 1H; 7.30, d, 1H; 7.40, t, 1H; 7.53, d, 1H; 7.80-7.88, m, 2H.

Example 18

Preparation of 2-[4-(2-Methoxyethoxy)phenyl]-6-propylsulfanyl-imidazo[1,2-b]pyridazine (Compound 65)

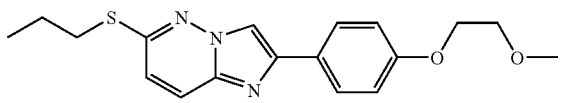

a) 6-Propylsulfanylpyridazin-3-amine was prepared by the procedure of Barlin and Ireland, *Australian Journal of Chemistry*, 1987, 40, 1491-7.

b) 2-Bromo-1-[4-(2-methoxyethoxy)phenyl]ethanone was prepared by the procedure of Ostermayer, Zimmermann and Fuhrer, UK Patent Application GB 2 065 645 A.

c) A solution of 6-propylsulfanylpyridazin-3-amine (169 mg, 1 mmol) and 2-bromo-1-[4-(2-methoxyethoxy)phenyl]ethanone (273 mg, 1 mmol) in ethanol (10 mL) was refluxed for 3 h. Sodium hydrogen carbonate (84 mg, 1 mmol) was then added and the mixture was refluxed for a further 3 h. The solvent was evaporated and the organic residue was extracted with chloroform. The chloroform extract was washed with water, dried (sodium sulfate) and evaporated. The residue was purified by radial chromatography on silica gel. Elution with 2-3% methanol in dichloromethane afforded Compound 65 (57 mg). $^1$H n.m.r. (CDCl$_3$) δ 1.12, t, J=6 Hz, 3H; 1.75-1.95, m, 2H; 3.16-3.22, m, 2H; 3.27, s, 3H; 3.75-3.82, m, 2H; 4.15-4.22, m, 2H; 6.88-7.08, m, 3H; 7.80-7.995, m, 3H; 8.06, s, 1H.

Example 19

The Following Assay Can be Used to Determine the Parasiticidal Activity of the Compounds of the Invention.

*Haemonchus Contortus* Larvacidal Assay: NemaTOX H.contortus Dose Response (00/0510)

Effect on larval development is determined in the assay described by Gill et al. (*International Journal of Parasitology*, 1995, 25, 463-470). Briefly, in this assay nematode eggs were applied to the surface of an agar matrix containing the test compound and then allowed to develop through to the L3, infective stage (6 days)

The wells for each dilution of every compound (from highest to lowest concentration) were inspected to determine the well number corresponding to the lowest concentration at which development was inhibited in 99% of the nematode larvae present. As the well numbers correspond to a two-fold serial dilution of each compound, a titre (dilution factor) is generated as $2^{n-1}$, where n is the well number. By dividing the highest concentration tested by the titre an LD$_{99}$ value can be obtained, representing the concentration required to inhibit development in 99% of the nematode larvae present.

The compounds supplied as solid and viscous liquids were dissolved in DMSO. Twelve serial 1/2 dilutions in DMSO solution were prepared from the stock solution, each of which was then diluted 1/5 with water. Aliquots (10 µl) of each dilution were transferred to the bioassay plates to give a final concentration range of 0.024 to 50 µg/ml.

In Tables 1, 2 and 3 the *Haemonchus contortus* LD$_{99}$ values for compounds in accordance with the present invention are listed, measured in micrograms/mL.

TABLE 1

Formula (I)

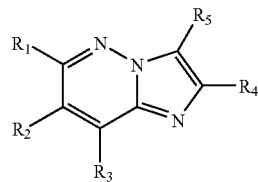

| Cd | R$_1$ | R$_2$ | R$_3$ | R$_4$ | R$_5$ | Mp ° C. | LD99 |
|---|---|---|---|---|---|---|---|
| 1 | methoxy | H | H | 4-methylphenyl | H | 139-140 | 3.75 |
| 2 | ethoxy | H | H | 4-methylphenyl | H | 139-140 | 0.875 |
| 3 | methylsulfanyl | H | H | phenyl | methoxy | 124.5-125.5 | 3 |
| 4 | methylsulfanyl | H | H | phenyl | H | 149-151 | 2.75 |
| 5 | phenylsulfanyl | H | H | phenyl | H | 127-129 | 1.625 |
| 6 | methylsulfanyl | H | H | 3,4-methylenedioxyphenyl | H | 162-163 | 3.25 |
| 7 | propylsulfanyl | H | H | 4-methylphenyl | H | 126-128 | 0.938 |
| 8 | propylsulfanyl | H | H | 3,4-methylenedioxyphenyl | H | 115-117 | 0.813 |
| 9 | methylsulfanyl | H | H | 2-(6-methyl)naphthyl | methoxy | 177-178 | >15.0 |
| 10 | benzyloxy | H | H | phenyl | H | 148-149 | 5.5 |
| 11 | propoxy | H | H | 4-chlorophenyl | H | 149-151 | 3.75 |
| 12 | ethylsulfanyl | H | H | 4-methylphenyl | H | 100-103 | 1.25 |
| 13 | propylsulfanyl | H | H | 3-methoxyphenyl | H | 138-140 | 0.63 |
| 14 | propylsulfanyl | H | H | 3,4,5-trimethoxyphenyl | H | 126-127 | >15.0 |
| 15 | methylsulfanyl | H | H | 3-methoxyphenyl | methoxy | 134-136 | 2.75 |
| 16 | propoxy | H | H | 3,4-methylendioxyphenyl | H | 125-126 | 0.23 |
| 17 | benzyloxy | H | H | 4-methoxyphenyl | methoxy | 132-134 | >15.0 |
| 18 | methoxy | H | H | 4-methoxyphenyl | H | 182 | 3 |
| 19 | (3-methoxyphenyl)sulfanyl | H | H | 3,4-methylenedioxyphenyl | H | | >15.0 |
| 20 | methylsulfanyl | H | H | 4-chlorophenyl | methylsulfanylmethyl | 127-128 | >15.0 |
| 21 | phenylsulfanyl | H | H | phenyl | methoxy | 150-151 | >15.0 |

TABLE 1-continued

Formula (I)

| Cd | R₁ | R₂ | R₃ | R₄ | R₅ | Mp °C. | LD99 |
|---|---|---|---|---|---|---|---|
| 22 | propylsulfanyl | H | H | phenyl | methoxy | 128-129 | >15.0 |
| 23 | benzyloxy | H | H | phenyl | methoxy | 143-144 | >15.0 |
| 24 | ethylsulfanyl | H | H | phenyl | methoxy | 86-87 | 7.5 |
| 25 | 2-methoxyethoxy | H | H | 3,4-methylenedioxyphenyl | H | | 1.25 |
| 26 | propoxy | H | H | 3,4-dimethoxyphenyl | H | | 1.3 |
| 27 | propoxy | H | H | 4-ethoxyphenyl | H | | 0.1 |
| 28 | propoxy | H | H | 3-methoxyphenyl | H | | 0.23 |
| 29 | propylsulfanyl | H | H | 3,4-dimethoxyphenyl | H | | 1.9 |
| 30 | propylsulfanyl | H | H | 4-ethoxyphenyl | H | | 0.38 |
| 31 | cyclopentyloxy | H | H | 4-ethoxyphenyl | H | | 0.875 |
| 32 | propoxy | methyl | H | 4-ethoxyphenyl | H | | 0.188 |
| 33 | cyclopropylmethoxy | H | H | 4-ethoxyphenyl | H | | 0.0254 |
| 34 | propoxy | H | H | 2-(5-chloro)thienyl | H | | 0.188 |
| 35 | phenyl | H | H | 4-ethoxyphenyl | H | | 10 |
| 36 | phenyl | H | H | 4-methoxyphenyl | methyl | | 0.8123 |
| 37 | propoxy | H | H | 4-methoxyphenyl | methyl | | 0.344 |
| 38 | propoxy | H | H | 3-bromo-4-methoxyphenyl | methyl | | 3.75 |
| 39 | cyclopropylmethoxy | H | H | 4-ethoxyphenyl | bromo | | 2.75 |
| 40 | propoxy | H | H | 4-ethoxyphenyl | bromo | | 0.344 |
| 41 | (4-methoxybenzyl)sulfanyl | H | H | 4-ethoxyphenyl | H | | 11 |
| 42 | (4-chlorobenzyl)sulfanyl | H | H | 4-ethoxyphenyl | H | | 3 |
| 43 | cyclopropylmethoxy | H | H | 3,4-methylenedioxyphenyl | H | | 0.117 |
| 44 | cyclopropylmethoxy | H | H | 2-thienyl | methyl | | 0.375 |
| 45 | bromo | H | H | 2-thienyl | methyl | | 6 |
| 46 | hexylsulfanyl | H | H | 2-thienyl | methyl | | 6.5 |
| 47 | (4-methoxybenzyl)sulfanyl | H | H | 2-thienyl | methyl | | 7.5 |
| 48 | propylsulfanyl | H | H | 4-ethoxyphenyl | chloro | | 6 |
| 49 | isobutylsulfanyl | H | H | 4-ethoxyphenyl | H | | 1.75 |
| 50 | isopropylsulfanyl | H | H | 4-ethoxyphenyl | H | | 0.875 |
| 51 | isopropoxy | H | H | 4-ethoxyphenyl | H | | 1.875 |
| 52 | isopropylsulfanyl | H | H | 4-methoxyphenyl | H | | 0.938 |
| 53 | butoxy | H | H | 4-propoxyphenyl | H | | 0.344 |
| 54 | propoxy | H | H | 2,4-difluorophenyl | H | | 0.219 |
| 55 | propoxy | H | H | 4-fluorophenyl | H | | 0.813 |
| 56 | cyclopropylmethoxy | H | H | 4-ethylphenyl | H | | 0.0781 |
| 57 | isobutylsulfanyl | H | H | 3,4-dimethoxyphenyl | H | | 1.375 |
| 58 | isopropoxy | H | H | 3,4-dimethoxyphenyl | H | | 15 |
| 59 | butoxy | H | H | 4-propoxyphenyl | dimethylaminomethyl | | 14 |
| 60 | ethoxy | H | H | 4-ethoxyphenyl | H | | 0.172 |
| 61 | propoxy | H | H | 2,3-dihydrobenzo[1,4]dioxin-6-yl | H | | 0.813 |
| 62 | propoxy | —CH═CH—CH═CH— | | 4-ethoxyphenyl | H | | 0.625 |

TABLE 2

Formula (I)

| Cd | R₁ | R₂ | R₃ | R₄ | R₅ | LD99 |
|---|---|---|---|---|---|---|
| 63 | propoxy | H | H | 4-(2-methoxyethoxy)phenyl | H | 0.0938 |
| 64 | 2-methoxyethoxy | H | H | 4-(2-methoxyethoxy)phenyl | H | 6 |
| 65 | propylsulfanyl | H | H | 4-(2-methoxyethoxy)phenyl | H | 0.81 |
| 66 | propoxy | H | H | 3-methoxy-4-(2-methoxyethoxy)phenyl | H | 0.81 |
| 67 | 1-piperidyl | H | H | 4-(2-methoxyethoxy)phenyl | H | 1.5 |

TABLE 2-continued

Formula (I)

| Cd | R₁ | R₂ | R₃ | R₄ | R₅ | LD99 |
|---|---|---|---|---|---|---|
| 68 | propylsulfanyl | H | H | 3-methoxy-4-(2-methoxyethoxy)phenyl | H | 0.44 |
| 69 | H | H | H | 4-(2-methoxyethoxy)phenyl | H | 15 |
| 70 | 1-pyrrolidinyl | H | H | 4-(2-methoxyethoxy)phenyl | H | 3.25 |
| 71 | propylamino | H | H | 4-(2-methoxyethoxy)phenyl | H | 0.688 |
| 72 | N-methylbutylamino | H | H | 4-(2-methoxyethoxy)phenyl | H | 0.813 |
| 73 | cyclopentyloxy | H | H | 4-(2-methoxyethoxy)phenyl | H | 1.875 |
| 74 | cyclopentyloxy | H | H | 4-(2-hydroxyethoxy)phenyl | H | 7 |
| 75 | cyclopropylmethoxy | H | H | 4-(2-methoxyethoxy)phenyl | H | 0.0391 |
| 76 | cyclopropylmethoxy | H | H | 4-(2-hydroxyethoxy)phenyl | H | 0.188 |
| 77 | propoxy | Me | H | 4-(2-methoxyethoxy)phenyl | H | 0.0586 |
| 78 | propoxy | Me | H | 4-(2-hydroxyethoxy)phenyl | H | 0.438 |
| 79 | phenyl | H | H | 4-ethoxyphenyl | H | 2.75 |
| 80 | 3-thienyl | H | H | 4-(2-methoxyethoxy)phenyl | H | 0.688 |
| 81 | propoxy | H | H | 4-(2-methoxyethoxy)phenyl | bromo | 0.0137 |
| 82 | butyl | H | H | 4-(2-methoxyethoxy)phenyl | H | 0.625 |
| 83 | propoxy | H | H | 3-bromo-4-(2-methoxyethoxy)phenyl | methyl | 0.375 |
| 84 | propoxy | H | H | 4-(2-methoxyethoxy)phenyl | methyl | 0.109 |
| 85 | phenyl | H | H | 4-(2-methoxyethoxy)phenyl | methyl | 1.88 |
| 86 | chloro | H | H | 3-bromo-4-(2-methoxyethoxy)phenyl | methyl | 3 |
| 87 | chloro | H | H | 4-(2-methoxyethoxy)phenyl | methyl | 0.156 |
| 88 | cyclopropylmethoxy | H | H | 4-(2-methoxyethoxy)phenyl | bromo | 0.0423 |
| 89 | propylsulfanyl | H | H | 3-methoxy-4-(2-methoxyethoxy)phenyl | bromo | 0.75 |
| 90 | bromo | H | H | 4-(2-methoxyethoxy)phenyl | H | 3 |
| 91 | propoxy | H | H | 4-(2-methoxyethoxy)phenyl | chloro | 0.0195 |
| 92 | benzyloxy | H | H | 4-(2-methoxyethoxy)phenyl | H | 0.438 |
| 93 | bromo | H | H | 3-(2-methoxyethoxy)phenyl | methyl | 11 |
| 94 | propoxy | H | H | 3-(2-methoxyethoxy)phenyl | methyl | 1.88 |
| 95 | cyclopropylmethoxy | H | H | 3-(2-methoxyethoxy)phenyl | methyl | 0.875 |
| 96 | propoxy | H | H | 4-(2-methoxyethoxy)phenyl | iodo | 0.0147 |
| 97 | propoxy | H | H | 4-(2-methoxyethoxy)phenyl | phenyl | 3.75 |
| 98 | propoxy | H | H | 4-(2-methoxyethoxy)phenyl | dimethylaminomethyl | 15 |
| 99 | butylsulfanyl | H | H | 4-(2-methoxyethoxy)phenyl | H | 0.0938 |
| 100 | ethoxy | H | H | 4-(2-methoxyethoxy)phenyl | H | 0.406 |
| 101 | ethylsulfanyl | H | H | 4-(2-methoxyethoxy)phenyl | H | 0.3123 |
| 102 | isobutylsulfanyl | H | H | 3-(2-methoxyethoxy)phenyl | methyl | 12 |
| 103 | isopropylsulfanyl | H | H | 3-(2-methoxyethoxy)phenyl | methyl | 7 |
| 104 | isopropoxy | H | H | 3-(2-methoxyethoxy)phenyl | methyl | 5 |
| 105 | isobutylsulfanyl | H | H | 3-methoxy-4-(2-methoxyethoxy)phenyl | H | 0.406 |
| 106 | butoxy | H | H | 3-methoxy-4-(2-methoxyethoxy)phenyl | H | 0.313 |
| 107 | isopropoxy | H | H | 3-methoxy-4-(2-methoxyethoxy)phenyl | H | 7 |
| 108 | isobutylsulfanyl | H | H | 4-(2-methoxyethoxy)phenyl | H | 0.313 |
| 109 | isopropylsulfanyl | H | H | 4-(2-methoxyethoxy)phenyl | H | 0.203 |
| 110 | propoxy | H | H | 4-(2-methoxyethoxy)phenyl | cyano | 0.0391 |
| 111 | butoxy | H | H | 4-(2-methoxyethoxy)phenyl | H | 0.219 |
| 112 | isopropoxy | H | H | 4-(2-methoxyethoxy)phenyl | H | 1.63 |
| 113 | propoxy | H | H | 3-methoxy-4-(2-methoxyethoxy)phenyl | I | 5 |
| 114 | isobutylsulfanyl | H | H | 4-(2-methoxyethoxy)phenyl | dimethylaminomethyl | 3.25 |
| 115 | butylsulfanyl | H | H | 4-(2-ethoxyethoxy)phenyl | H | 0.219 |
| 116 | propoxy | H | H | 4-(2-ethoxyethoxy)phenyl | H | 0.109 |
| 117 | cyclopropylmethoxy | H | H | 4-(2-ethoxyethoxy)phenyl | H | 0.0391 |
| 118 | ethoxy | H | H | 3-methoxy-4-(2-methoxyethoxy)phenyl | H | 1.25 |
| 119 | propoxy | —CH=CH—CH=CH— | | 4-(2-methoxyethoxy)phenyl | H | 0.344 |
| 120 | propoxy | —CH=CH—CH=CH— | | 4-(2-hydroxyethoxy)phenyl | H | 1.38 |

TABLE 3

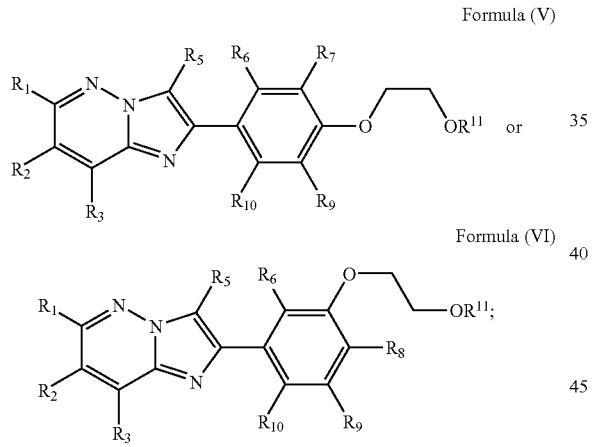

| Cd | R₁ | m | R₈ | LD99 |
|---|---|---|---|---|
| 121 | propoxy | 2 | methoxy | 0.203 |
| 122 | cyclopropylmethoxy | 2 | methoxy | 0.0938 |
| 123 | propoxy | 1 | H | 0.469 |
| 124 | ethylsulfanyl | 2 | methoxy | 1.5 |
| 125 | ethylsulfanyl | 1 | H | 1.38 |
| 126 | butylsulfanyl | 2 | methoxy | 1.88 |

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

What is claimed is:

1. An imidazo[1,2-b]pyridazine compound comprising the chemical formula:

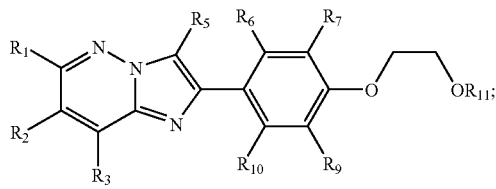

or a pharmaceutically-acceptable salt thereof, wherein:
$R_1$ is hydrogen, $(C_1-C_6)$alkoxy, $(C_3-C_{10})$cycloalkoxy, $(C_3-C_{10})$cycloalkyl $(C_1-C_6)$alkoxy, aryloxy, aryl $(C_1-C_6)$alkoxy, $(C_1-C_6)$alkoxy$(C_1-C_6)$alkoxy, aryloxy$(C_1-C_6)$alkoxy, arylsulfanyl $(C_1-C_6)$alkyloxy, $(C_1-C_6)$alkylsulfanyl, arylsulfanyl, aryl$(C_1-C_6)$alkylsulfanyl, or $(C_1-C_6)$alkyl, $(C_3-C_{10})$cycloalkyl, aryl, heteroaryl, aryl$(C_1-C_6)$alkyl, heterocyclyl, halo, amino, $(C_1-C_6)$alkylamino, $(C_1-C_6)$dialkylamino, or arylamino;
$R_2$, $R_3$ and $R_5$ are independently selected from hydrogen, $(C_1-C_6)$alkyl, aryl, $(C_1-C_6)$alkylsulfanylmethyl, $(C_1-C_6)$dialkylaminomethyl, cyano, and halo;
$R_6$, $R_7$, $R_8$, $R_9$ and $R_{10}$ are independently selected from hydrogen, $(C_1-C_6)$alkyl, halo, $(C_1-C_6)$alkoxy, $(C_1-C_6)$alkoxy$(C_1-C_6)$alkoxy, and hydroxy$(C_1-C_6)$alkoxy; and
$R_{11}$ is hydrogen or $(C_1-C_6)$alkyl.

2. The imidazo[1,2-b]pyridazine compound of claim 1, comprising the chemical formula:

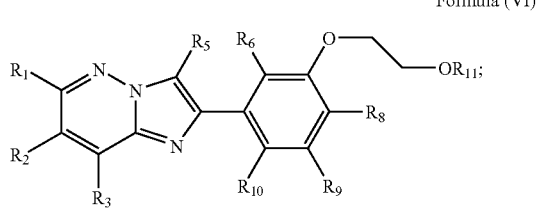

or a pharmaceutically-acceptable salt thereof, wherein:
$R_1$ is hydrogen, $(C_1-C_6)$alkoxy, $(C_3-C_{10})$cycloalkoxy, $(C_3-C_{10})$cycloalkyl $(C_1-C_6)$alkoxy, aryloxy, aryl $(C_1-C_6)$alkoxy, $(C_1-C_6)$alkoxy, arylsulfanyl, aryl$(C_1-C_6)$alkylsulanyl, or $(C_1-C_6)$alkyl, $(C_3-C_{10})$cycloalkyl, aryl, heteroaryl, aryl$(C_1-C_6)$alkyl, heterocyclyl, halo, amino, $(C_1-C_6)$alkylamino, $(C_1-C_6)$dialkylamino, or arylamino;
$R_2$, $R_3$ and $R_5$ are independently selected from hydrogen, $(C_1-C_6)$alkyl, aryl, $(C_1-C_6)$alkylsulfanylmethyl, $(C_1-C_6)$dialkylaminomethyl, cyano, and halo;
$R_6$, $R_7$, $R_8$, $R_9$ and $R_{10}$ are independently selected from hydrogen, $(C_1-C_6)$alkyl, halo, $(C_1-C_6)$alkoxy, $(C_1-C_6)$alkoxy$(C_1-C_6)$alkoxy, and hydroxy$(C_1-C_6)$alkoxy; and
$R_{11}$ is hydrogen or $(C_1-C_6)$alkyl.

3. The imidazo[1,2-b]pyridazine compound of claim 1, comprising the chemical formula:

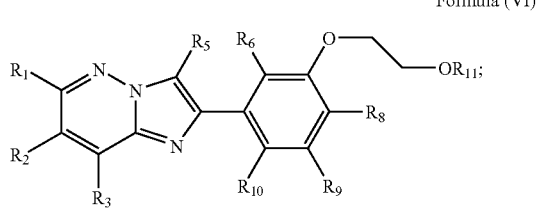

or a pharmaceutically-acceptable salt thereof, wherein:
$R_1$ is hydrogen, $(C_1-C_6)$alkoxy, $(C_3-C_{10})$cycloalkoxy, $(C_3-C_{10})$cycloalkyl $(C_1-C_6)$alkoxy, aryloxy, aryl $(C_1-C_6)$alkoxy, $(C_1-C_6)$alkoxy, $(C_1-C_6)$alkoxy, aryloxy$(C_1-C_6)$alkoxy, arylsulfanyl $(C_1-C_6)$alkyloxy, $(C_1-C_6)$alkylsulfanyl, arylsufanyl, aryl$(C_1-C_6)$alkylsulanyl, or $(C_1-C_6)$alkyl, $(C_3-C_{10})$cycloalkyl, aryl, heteroaryl, aryl$(C_1-C_6)$alkyl, heterocyclyl, halo, amino, $(C_1-C_6)$alkylamino, $(C_1-C_6)$dialkylamino, or arylamino;
$R_2$, $R_3$ and $R_5$ are independently selected from hydrogen, $(C_1-C_6)$alkyl, aryl, $(C_1-C_6)$alkylsulfanylmethyl, $(C_1-C_6)$dialkylaminomethyl, cyano, and halo;
$R_6$, $R_7$, $R_8$, $R_9$ and $R_{10}$ are independently selected from hydrogen, $(C_1-C_6)$alkyl, halo, $(C_1-C_6)$alkoxy, $(C_1-C_6)$alkoxy$(C_1-C_6)$alkoxy, and hydroxy$(C_1-C_6)$alkoxy; and
$R_{11}$ is hydrogen or $(C_1-C_6)$alkyl.

4. A pharmaceutical composition comprising a therapeutically effective dosage amount of the compound of claim 1 and a pharmaceutically acceptable excipient.

5. An imidazo[1,2-b]pyridazine compound comprising the chemical formula of Formula (I):

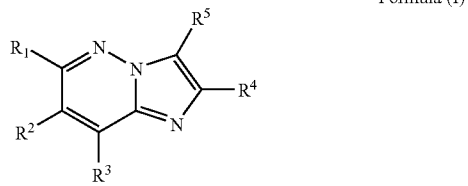

or a pharmaceutically-acceptable salt thereof,
wherein $R_1$, $R_2$, $R_3$, $R_4$ and $R_5$ for each compound are defined as follows:

| Cd | R₁ | R₂ | R₃ | R₄ | R₅ |
|---|---|---|---|---|---|
| 63 | propoxy | H | H | 4-(2-methoxyethoxy)phenyl | H |
| 64 | 2-methoxyethoxy | H | H | 4-(2-methoxyethoxy)phenyl | H |
| 65 | propylsulfanyl | H | H | 4-(2-methoxyethoxy)phenyl | H |
| 66 | propoxy | H | H | 3-methoxy-4-(2-methoxyethoxy)phenyl | H |
| 67 | 1-piperidyl | H | H | 4-(2-methoxyethoxy)phenyl | H |
| 68 | propylsulfanyl | H | H | 3-methoxy-4-(2-methoxyethoxy)phenyl | H |
| 69 | H | H | H | 4-(2-methoxyethoxy)phenyl | H |
| 70 | 1-pyrrolidinyl | H | H | 4-(2-methoxyethoxy)phenyl | H |
| 71 | propylamino | H | H | 4-(2-methoxyethoxy)phenyl | H |
| 72 | N-methylbutylamino | H | H | 4-(2-methoxyethoxy)phenyl | H |
| 73 | cyclopentyloxy | H | H | 4-(2-methoxyethoxy)phenyl | H |
| 74 | cyclopentyloxy | H | H | 4-(2-hydroxyethoxy)phenyl | H |
| 75 | cyclopropylmethoxy | H | H | 4-(2-methoxyethoxy)phenyl | H |
| 76 | cyclopropylmethoxy | H | H | 4-(2-hydroxyethoxy)phenyl | H |
| 77 | propoxy | Me | H | 4-(2-methoxyethoxy)phenyl | H |
| 78 | propoxy | Me | H | 4-(2-hydroxyethoxy)phenyl | H |
| 79 | phenyl | H | H | 4-ethoxyphenyl | H |
| 80 | 3-thienyl | H | H | 4-(2-methoxyethoxy)phenyl | H |
| 81 | propoxy | H | H | 4-(2-methoxyethoxy)phenyl | bromo |
| 82 | butyl | H | H | 4-(2-methoxyethoxy)phenyl | H |
| 83 | propoxy | H | H | 3-bromo-4-(2-methoxyethoxy)phenyl | methyl |
| 84 | propoxy | H | H | 4-(2-methoxyethoxy)phenyl | methyl |
| 85 | phenyl | H | H | 4-(2-methoxyethoxy)phenyl | methyl |
| 86 | chloro | H | H | 3-bromo-4-(2-methoxyethoxy)phenyl | methyl |
| 87 | chloro | H | H | 4-(2-methoxyethoxy)phenyl | methyl |
| 88 | cyclopropylmethoxy | H | H | 4-(2-methoxyethoxy)phenyl | bromo |
| 89 | propylsulfanyl | H | H | 3-methoxy-4-(2-methoxyethoxy)phenyl | bromo |
| 90 | bromo | H | H | 4-(2-methoxyethoxy)phenyl | H |
| 91 | propoxy | H | H | 4-(2-methoxyethoxy)phenyl | chloro |
| 92 | benzyloxy | H | H | 4-(2-methoxyethoxy)phenyl | H |
| 93 | bromo | H | H | 3-(2-methoxyethoxy)phenyl | methyl |
| 94 | propoxy | H | H | 3-(2-methoxyethoxy)phenyl | methyl |
| 95 | cyclopropylmethoxy | H | H | 3-(2-methoxyethoxy)phenyl | methyl |
| 96 | propoxy | H | H | 4-(2-methoxyethoxy)phenyl | iodo |
| 97 | propoxy | H | H | 4-(2-methoxyethoxy)phenyl | phenyl |
| 98 | propoxy | H | H | 4-(2-methoxyethoxy)phenyl | dimethylaminomethyl |
| 99 | butylsulfanyl | H | H | 4-(2-methoxyethoxy)phenyl | H |
| 100 | ethoxy | H | H | 4-(2-methoxyethoxy)phenyl | H |
| 101 | ethylsulfanyl | H | H | 4-(2-methoxyethoxy)phenyl | H |
| 102 | isobutylsulfanyl | H | H | 3-(2-methoxyethoxy)phenyl | methyl |
| 103 | isopropylsulfanyl | H | H | 3-(2-methoxyethoxy)phenyl | methyl |
| 104 | isopropoxy | H | H | 3-(2-methoxyethoxy)phenyl | methyl |
| 105 | isobutylsulfanyl | H | H | 3-methoxy-4-(2-methoxyethoxy)phenyl | H |
| 106 | butoxy | H | H | 3-methoxy-4-(2-methoxyethoxy)phenyl | H |
| 107 | isopropoxy | H | H | 3-methoxy-4-(2-methoxyethoxy)phenyl | H |
| 108 | isobutylsulfanyl | H | H | 4-(2-methoxyethoxy)phenyl | H |
| 109 | isopropylsulfanyl | H | H | 4-(2-methoxyethoxy)phenyl | H |
| 110 | propoxy | H | H | 4-(2-methoxyethoxy)phenyl | cyano |
| 111 | butoxy | H | H | 4-(2-methoxyethoxy)phenyl | H |
| 112 | isopropoxy | H | H | 4-(2-methoxyethoxy)phenyl | H |
| 113 | propoxy | H | H | 3-methoxy-4-(2-methoxyethoxy)phenyl | I |
| 114 | isobutylsulfanyl | H | H | 4-(2-methoxyethoxy)phenyl | dimethylaminomethyl |
| 115 | butylsulfanyl | H | H | 4-(2-ethoxyethoxy)phenyl | H |
| 116 | propoxy | H | H | 4-(2-ethoxyethoxy)phenyl | H |
| 117 | cyclopropylmethoxy | H | H | 4-(2-ethoxyethoxy)phenyl | H |
| 118 | ethoxy | H | H | 3-methoxy-4-(2-methoxyethoxy)phenyl | H. |

6. A method of treatment of *Haemonchus contortus* infestation in animals, comprising administering to an animal inneed of such treatment an effective amount of the imidazo[1,2-b]pyridazine compound of claim 5.

* * * * *